(12) United States Patent
Callaway et al.

(10) Patent No.: US 7,166,132 B2
(45) Date of Patent: Jan. 23, 2007

(54) ADJUSTABLE BONE PROSTHESES AND RELATED METHODS

(75) Inventors: George Hadley Callaway, Raleigh, NC (US); Dennis M McDevitt, Raleigh, NC (US)

(73) Assignee: IncuMed, Inc., Raleigh, NC (US)

( * ) Notice: Subject to any disclaimer, the term of this patent is extended or adjusted under 35 U.S.C. 154(b) by 0 days.

(21) Appl. No.: 10/767,673

(22) Filed: Jan. 29, 2004

(65) Prior Publication Data

US 2004/0186579 A1   Sep. 23, 2004

Related U.S. Application Data

(62) Division of application No. 10/041,722, filed on Jan. 8, 2002, now Pat. No. 6,736,852.

(60) Provisional application No. 60/271,895, filed on Feb. 27, 2001.

(51) Int. Cl.
*A61F 2/40* (2006.01)
(52) U.S. Cl. .................. 623/23.47; 623/19.11; 623/22.11; 403/119; 403/121; 403/123
(58) Field of Classification Search ............ 623/16.11, 623/18.11, 19.1–19.14, 22.11, 23.37; 403/119, 403/121, 123
See application file for complete search history.

(56) References Cited

U.S. PATENT DOCUMENTS

| 362,384 | A | | 5/1887 | Johnson |
|---|---|---|---|---|
| 1,446,164 | A | | 2/1923 | D'Eyraud |
| 1,538,340 | A | | 5/1925 | La Hodny |
| 3,671,978 | A | * | 6/1972 | May .............................. 623/38 |
| 4,051,924 | A | | 10/1977 | Yoshigai |
| 4,475,314 | A | | 10/1984 | Faix et al. |
| 4,536,898 | A | * | 8/1985 | Palfray ......................... 623/33 |
| 4,669,766 | A | | 6/1987 | Hanchett, Jr. et al. |
| 4,722,502 | A | | 2/1988 | Mueller et al. |
| 5,195,710 | A | | 3/1993 | Remblier |
| 5,425,782 | A | | 6/1995 | Phillips |
| 5,545,230 | A | * | 8/1996 | Kinsinger et al. ............ 623/38 |
| 5,562,737 | A | | 10/1996 | Graf |
| 5,623,742 | A | | 4/1997 | Journee et al. |
| 5,723,018 | A | | 3/1998 | Cyprien et al. |
| 5,725,597 | A | | 3/1998 | Hwang |
| 5,727,569 | A | | 3/1998 | Benetti et al. |
| 5,895,428 | A | | 4/1999 | Berry |
| 5,921,695 | A | | 7/1999 | Warner |
| 6,083,263 | A | | 7/2000 | Draenert et al. |
| 6,123,706 | A | | 9/2000 | Lange |
| 6,171,039 | B1 | | 1/2001 | Seurujarvi |

(Continued)

FOREIGN PATENT DOCUMENTS

EP   0 791 330   8/1997

(Continued)

*Primary Examiner*—Bruce Snow
*Assistant Examiner*—Cheryl Miller
(74) *Attorney, Agent, or Firm*—Ryan Kromholz & Manion, S.C.

(57) ABSTRACT

Adjustable prostheses and related methods provide a wide range of adjustment along or about multiple axes. The prostheses and related methods make possible a straightforward, yet robust way of securing, e.g., a humeral head prosthesis in a desired position and maintaining the prosthesis in the desired position during use.

2 Claims, 34 Drawing Sheets

U.S. PATENT DOCUMENTS

| | | |
|---|---|---|
| 6,197,063 B1 | 3/2001 | Dews |
| 6,228,120 B1 | 5/2001 | Leonard et al. |
| 6,241,730 B1 | 6/2001 | Alby |
| 6,248,132 B1 | 6/2001 | Harris |
| 6,273,390 B1 | 8/2001 | Meyer |
| 6,302,887 B1 | 10/2001 | Spranza et al. |
| 6,387,130 B1 * | 5/2002 | Stone et al. ............. 623/17.16 |
| 6,409,766 B1 * | 6/2002 | Brett ....................... 623/17.16 |
| 6,736,852 B1 * | 5/2004 | Callaway et al. ........ 623/19.14 |
| 6,755,862 B1 * | 6/2004 | Keynan ................... 623/16.11 |
| 6,887,279 B1 * | 5/2005 | Phillips et al. ................ 623/38 |
| 6,896,436 B1 * | 5/2005 | McDevitt .................... 403/123 |
| 2004/0143341 A1 * | 7/2004 | McLean .................. 623/22.15 |

FOREIGN PATENT DOCUMENTS

| | | |
|---|---|---|
| EP | 0 920 835 | 6/1999 |
| WO | WO 98/08468 | 3/1998 |
| WO | WO 98/49947 | 4/1998 |
| WO | WO 99/16367 | 4/1999 |
| WO | WO 00/15119 | 3/2000 |
| WO | WO 01/06909 | 2/2001 |

* cited by examiner

ADJUSTABLE BONE PROSTHESES AND RELATED METHODS

RELATED APPLICATIONS

This application is a divisional of co-pending U.S. application Ser. No. 10/041,722, filed on 8 Jan. 2002, which claims the benefit of provisional Application Ser. No. 60/271,895, filed on 27 Feb. 2001, entitled "Adjustable Head Prosthesis for the Shoulder."

FIELD OF THE INVENTION

This invention generally relates to an adjustable mounting assembly and alignment system for a bone prosthesis and related methods.

BACKGROUND OF THE INVENTION

A shoulder joint consists of a ball-and-socket type coupling of the humerus to the scapula. The humerus forms the ball, and the socket is formed at the glenoid cavity of the scapula. Injury or disease to the joint often results in destruction or deterioration of the head of the humerus, leading to pain and a corresponding loss of mobility and function. In such cases, it is often necessary to provide a replacement joint surface, i.e., a prosthesis, for the head of the humerus that mates with the glenoid cavity.

The proper alignment of the prosthesis is generally useful to effective performance of the replacement procedure. Typically, the position of the mount is adjusted until the desired position is achieved. The mount is fixed in the desired position and the prosthesis is then secured onto the mount.

However, conventional mounts provide only a limited range of adjustment, typically allowing only two degrees of freedom, i.e., linearly along an X-axis and Y-axis. The devices that do have more degrees of freedom require multiple trials and a fixture to be used away from the surgical site for proper alignment of the prosthesis to the humerus.

Further, even upon locking the device in a desired position, conventional mounts may not hold the desired position. This is especially true when force is exerted, e.g., hammering the prosthesis to secure its placement on a mount.

There remains a need for mounting systems and methods that permit a wide range of adjustment of a humeral head prosthesis while enabling the mount, and attached prosthesis, to remain securely fixed in a desired position.

SUMMARY OF THE INVENTION

The invention provides various adjustable prostheses and related methods that provide a wide range of adjustment along or about multiple axes. The invention makes possible a straightforward, yet robust way of securing, e.g., a humeral head prosthesis in a desired position and maintaining the prosthesis in the desired position during use.

Other features and advantages of the inventions are set forth in the following specification and attached drawings.

The invention may be embodied in several forms without departing from its spirit or essential characteristics. The scope of the invention is defined in the appended claims, rather than in the specific description preceding them. All embodiments that fall within the meaning and range of equivalency of the claims are therefore intended to be embraced by the claims.

DETAILED DESCRIPTION

Although the disclosure hereof is detailed and exact to enable those skilled in the art to practice the invention, the physical embodiments herein disclosed merely exemplify the invention that may be embodied in other specific structure. While the preferred embodiment has been described, the details may be changed without departing from the invention, which is defined by the claims.

I. The Adjustable Locking Mount System

A. System 1:

Interior Hub Centrally Located with Respect to Mounting Surface

Figure 1:
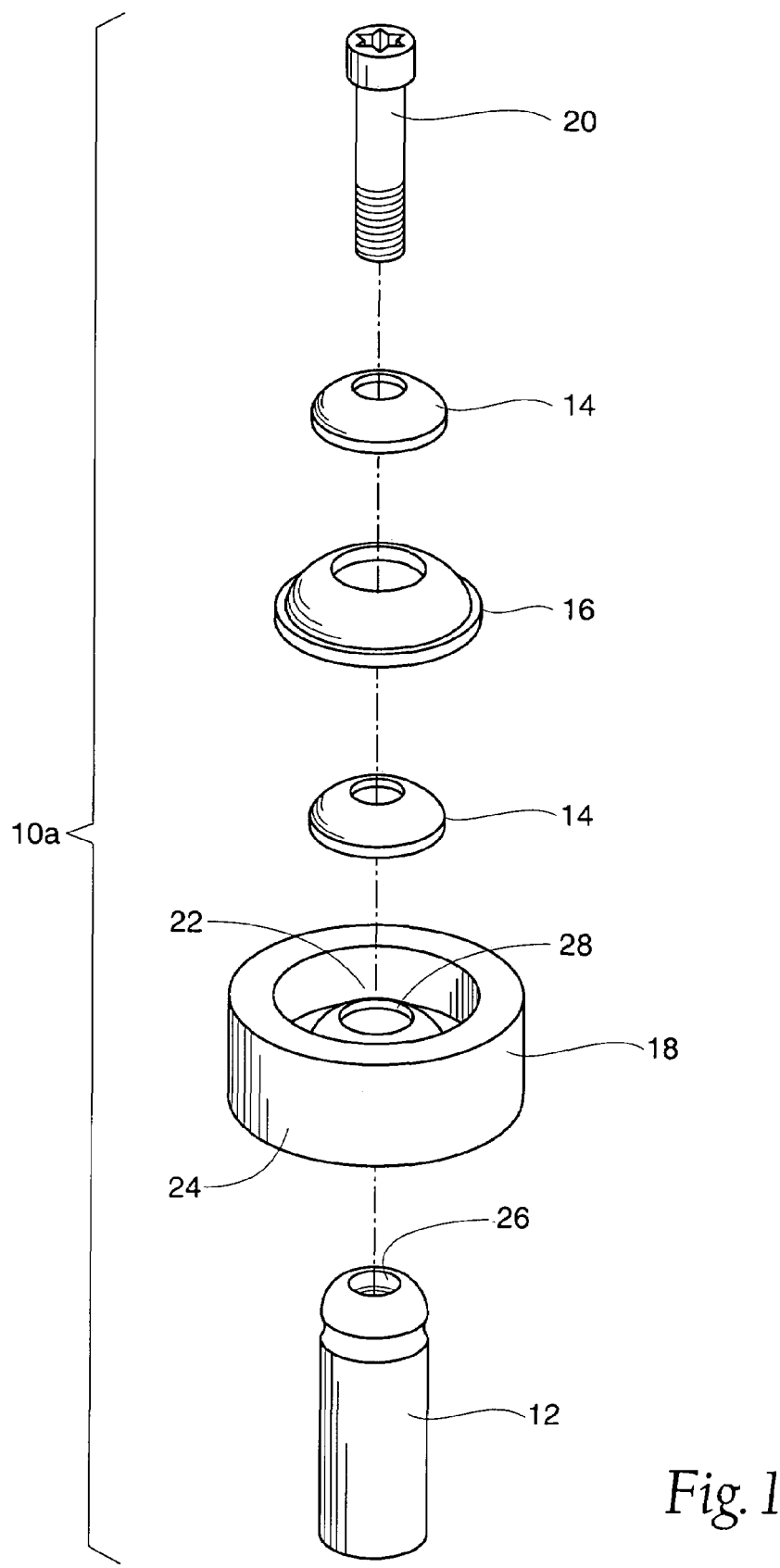
FIG. 1 is an exploded view of the components of an adjustable locking mount system that embodies features of the invention, in which the mounting hub is centric.
Figure 2:
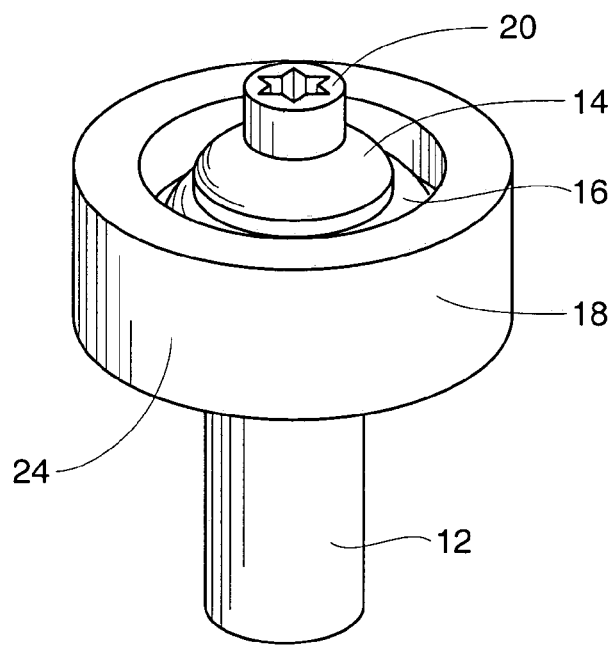
FIG. 2 is an assembled perspective view of the system shown in FIG. 1.
Figure 3A:
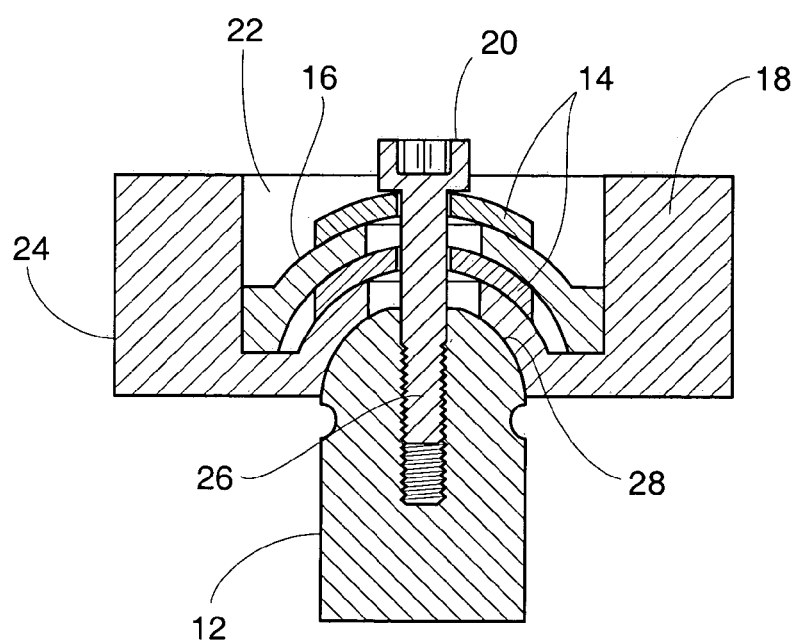
FIG. 3a is a side sectional view of the assembled components of the system shown in FIG. 2.

FIG. 1 shows the individual components of an adjustable locking mounting system 10A. FIGS. 2 and 3a illustrate the system 10A when assembled. As will be described in detail later, the system 10A permits adjustment in three directions or three degrees of freedom (rotational around axes x, y, and z, where the z-axis is represented by the axis of the pivot pin 12) (see FIGS. 4a–4e).

The system 10A comprises the pivot pin 12, at least one slip washer 14, at least one lock washer 16, a mounting hub 18, and a locking screw 20. Each of these components of the system 10A will now be described in detail.

1. System Components

As seen in FIG. 1, the pivot pin 12 is a rigid, generally cylindrical or rod-like member. The pivot pin 12 is convex, e.g., domed, at one end to couple with the mounting hub 18 (see, e.g., FIG. 3a). In a representative embodiment, the arc of curvature is 0.400" diameter (0.200" radius).

In particular, the convex arrangement permits adjustment of the mounting hub 18 by swinging or tilting across the axis of the pivot pin 12 (i.e., rotation about the x-axis and y-axis) as well as by rotating or twisting about the axis of the pivot pin 12 (i.e., rotation about the z-axis) (see FIGS. 4a–4e).

As best seen in FIGS. 1 and 3, the pivot pin 12 has a threaded central bore 26 that serves to receive the locking screw 20. Thus, the pivot pin 12 serves to receive both the mounting hub 18 and the locking screw 20 (see FIG. 3a).

The pivot pin 12 can be made of suitable metal, plastic, or ceramic materials and formed by conventional molding or machining techniques.

As shown in FIG. 1, the mounting hub 18 is a rigid member comprising a mounting surface 24, an interior hub 22, and an exterior pivot surface 28. The center of the mounting hub 18 serves to receive the locking screw 20.

The mounting surface 24 is configured to mate with an object or device being mounted on the hub and therefore can take on a variety of shapes. Thus, the mounting hub 18 serves as a base for mounting of another object or device. For example, the mounting surface 24 can be circular or geometric. In the illustrated embodiment, the mounting surface 24 is generally circular.

Additionally, the mounting surface 24 can be stepped to further aid in positioning and securing the object or device on the mounting surface 24 (not shown). In this arrangement, the object or device being mounted would have a complementary stepped surface. The stepped surface provides greater control of any adjustment by permitting adjustment to be in uniform increments and reducing the risk of inadvertent movement. The mounting surface 24 could alternatively be a threaded surface to facilitate engagement with a mating part.

As best illustrated in FIG. 1, the interior hub 22 is open. The bottom surface of the interior hub 22 is configured to conform to the shape of the convex end of the pivot pin 12 and sized to receive the slip washer(s) 14 and lock washer(s) 16. That is, the interior hub 22 permits a slip washer 14 and lock washer 16, or multiple slip washers 14 and lock washers 16, to be alternately stacked upon one another (see FIG. 3*a*).

As shown in FIGS. 1–3*a*, the exterior pivot surface 28 of the mounting hub 18 is configured to nest on and to conform to the convex end of the pivot pin 12, thus permitting a wider range of motion, as previously described.

As best seen in FIG. 3*a*, the exterior pivot surface 28 is located centrally with respect to the interior hub 22. Further, the interior hub 22 is centrally located with respect to the mounting surface 24, such that the geometric center of the mounting hub 18 coincides with the center of rotation of the mounting hub 18 about the pivot pin 12.

The mounting hub 18 serves to engage and pivot about the pivot pin 12, thus permitting adjustment of the position of the mounting hub 18 with respect to the pivot pin 12, as will be described later. Upon obtaining the desired position, the position of the mounting hub 18 can be locked by use of the locking screw 20, as will also be described in greater detail later.

The mounting hub 18 can be made of any suitable metal or plastic and formed by conventional machining or molding techniques.

As shown in FIG. 1, the system 10A also provides at least one slip washer 14. The slip washer 14 is preferably a rigid annular ring or doughnut-like member. As FIGS. 1 and 3*a* best show, the slip washer 14 is configured to conform to the bottom surface of the interior hub 22.

The center of the slip washer 14 serves to receive the locking screw 20. The center of the slip washer 14 is of a diameter only slightly larger than the outside diameter of the locking screw 20. The slip washer 14 also serves to provide a frictional surface, which upon tightening of the locking screw 20, serves to further secure the mounting hub 18 in a desired position.

Figure 5A:
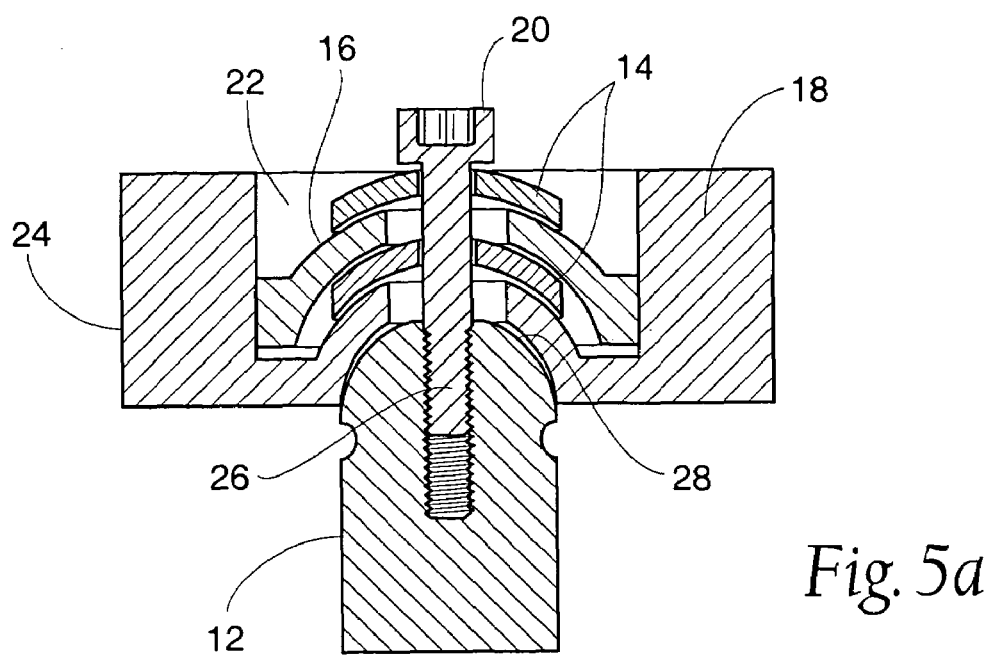
FIG. 5a is a side sectional view of the assembled components of the system shown in FIG. 3 and illustrating the system components in a level position.
Figure 5B:
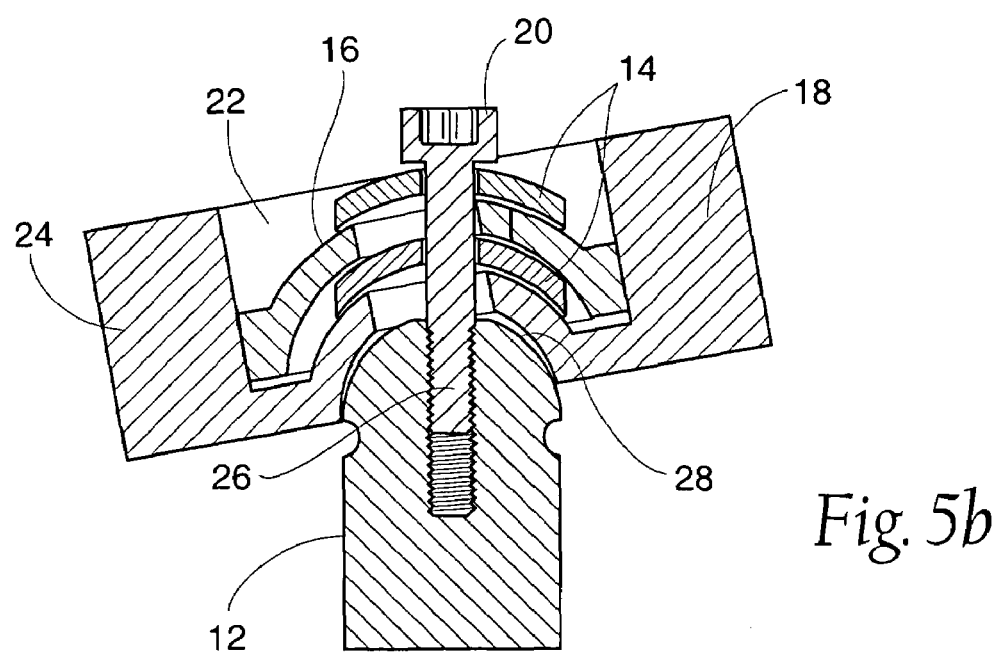
FIG. 5b is a sectional view as shown in FIG. 5a, illustrating the position of the system components and the movement of the mounting hub and lock washer when the mounting hub is rotated about the x or y axis.

The slip washer 14 permits the lock washer 16 to slide across the surface of the slip washer 14 (see FIGS. 5*a* and 5*b*). The slip washer 14 is similar in function yet physically different in top and bottom spherical radii from the lock washer 16.

Figure 3B:
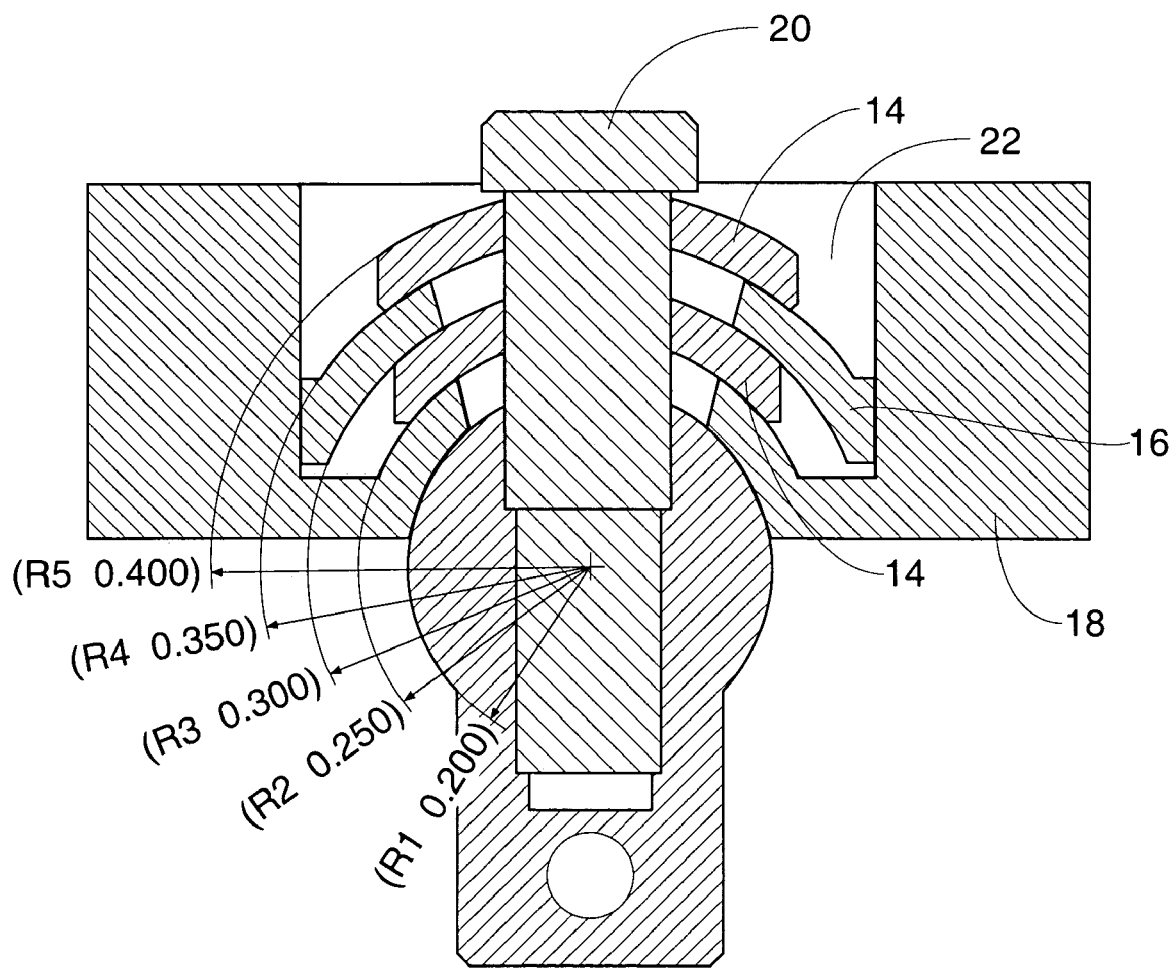
FIG. 3b is a view similar to FIG. 3a and illustrating the spherical radii of the stacked washers.

As seen in FIG. 3*b*, additional washers 14 and 16 in the assembly would also have different spherical radii, represented by R1–R5 in FIG. 3*b*, as they are stacked further from the center of rotation or pivot point on the pivot pin 12. In a representative embodiment, R1 is 0.200, R2 is 0.250, R3 is 0.300, R4 is 0.350, and R5 is 0.400.

The radii of the washers 14 and 16 can be varied to accommodate the thickness of the individual washers 14 and 16. Regardless of the thickness or radii of the washers 14 and 16, the washers 14 and 16 are configured to rotate about the same pivot point.

Desirably, as illustrated in FIGS. 1 and 3*a*, a second slip washer 14, similar in function but differing in spherical radii from the first slip washer 14 is placed over the lock washer 16. As illustrated in FIGS. 5*a* and 5*b*, the lock washer 16 is able to slide between the slip washers 14.

In this arrangement, the second slip washer 14 provides an additional frictional surface, which upon tightening of the locking screw 20, serves to further secure the desired position.

The slip washer(s) 14 can be made of any suitable metal or plastic and formed by conventional machining or molding techniques.

As also seen in FIG. 1, the system 10A further provides a lock washer 16. The lock washer 16 is a rigid, annular ring or doughnut-like member similar to the slip washer 14.

As FIGS. 1 and 3*a* best illustrate, the lock washer 16 is configured to conform to the surface of the slip washer 14. This arrangement permits the lock washer 16 to be stacked on top of the slip washer 14.

As in the case of the slip washer 14, the center of the lock washer 16 serves to receive the locking screw 20. The center of the lock washer 16 is also sized larger than the center of the slip washer 14. That is, the center of the lock washer 16 not only serves to receive the locking screw 20, but also permits the lock washer 16 to pivot about the pivot pin 12.

The lock washer 16 also provides two additional frictional surfaces when sandwiched between two slip washers 14, which upon tightening of the locking screw 20, serve to further secure the desired position.

As also seen in FIGS. 1 and 3*a*, the lock washer 16 is of a larger diameter than the slip washer 14. This arrangement allows the lock washer 16 to fit over the slip washer 14. In a representative embodiment, the lock washer 16 is sized to approximate or be slightly less than the diameter of the interior hub 22, thereby providing a secure fit of the lock washer 16 within the interior hub 22 and allowing only minimal translation in the x and y axes, yet not restricting z-axis translation of the lock washer 16 within the interior hub 22 and with respect to the axis of the pivot pin 12, as will later be described in detail.

This arrangement secures/couples the lock washer 16 to the interior hub 22 and permits the lock washer 16 to slide with the mounting hub 18 over the slip washer 14 (see, e.g., FIGS. 5*a* and 5*b*). Thus, the lock washer 16 serves to provide an additional rotational and rocking surface for the mounting hub 18.

Like the slip washer 14, the lock washer 16 can be made of any suitable plastic or metal and formed by conventional molding or machining techniques.

Desirably, as previously noted, a second slip washer 14 similar in function but differing in spherical radii from the first slip washer 14 can be provided. In this arrangement, as seen in FIGS. 1 and 3*a*, the lock washer 16 also serves to receive the second slip washer 14. It will be apparent that any number of slip washers 14 and lock washers 16 can be similarly alternately stacked upon each other and thereby accommodate variations in the depth of the interior hub 22.

As also shown in FIG. 1, the system 10A provides a locking screw 20. The locking screw 20 is a screw that is adapted for passage through the mounting hub 18, the slip washer(s) 14, the lock washer(s) 16, and the pivot pin 12 when the system is assembled (see FIG. 3*a*). In inside the diameter of the slip washer 14 is sized to approximate or be slightly larger than the diameter of the locking screw 20. This arrangement secures/couples the slip washer 14 to the locking screw 20 and the pivot pin 12.

Figure 5C:
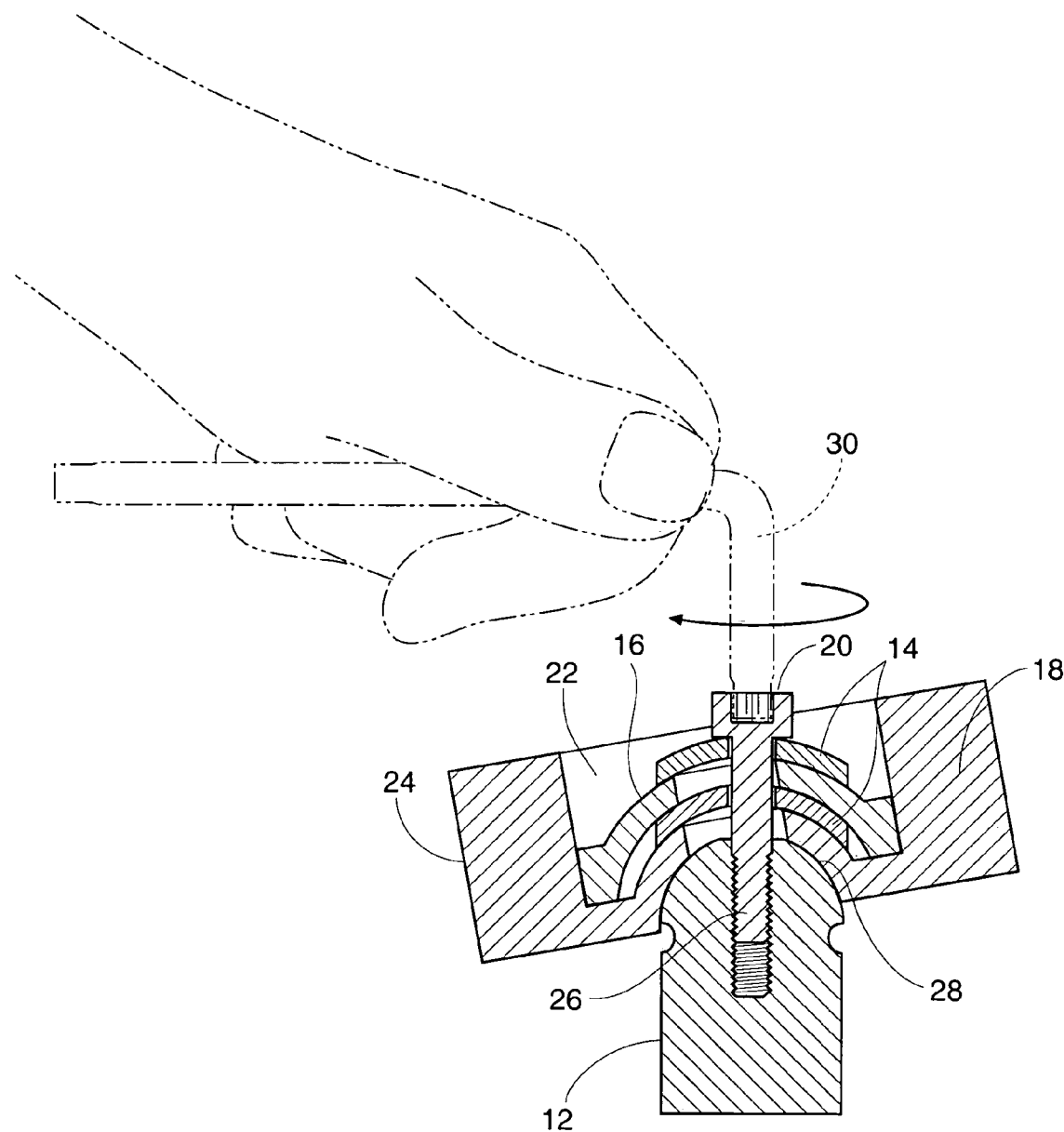
FIG. 5c is a sectional view as shown in FIG. 5b, illustrating the procedure of locking the system in a desired position.

As illustrated in FIG. 3a, the locking screw 20 is desirably threaded to fit the threaded bore 26 of the pivot pin 12. As FIG. 5c illustrates, rotation (represented by arrow in FIG. 5c) of the screw 20, e.g., by an Allen wrench 30, advances the screw into the pivot pin 12 to fix the mounting hub 18 in a desired position.

The locking screw 20 can be made of any suitable plastic or metal and formed by conventional molding or machining techniques.

The locking screw 20, when not fully tightened, serves to hold the assembly while the desired position is determined. Tightening of the locking screw 20 compresses the washers 14 and 16, hub 18, and pin 12 together, thereby creating multiple frictional forces between the mating surfaces. These frictional forces and the compression of the screw 20 are what limit movement in the locked position.

It will be apparent that the components just described can be used in any combination. For example, plastic slip washers 14 may be alternated with metal lock washers 16.

2. Adjustment of the Orientation of the Mounting Hub

The system 10A as previously described enables the mounting hub 18 to be oriented in a variety of directions with respect to the pivot pin 12. The types of movement, and thus the types of adjustments permitted, will now be discussed.

The system 10A permits movement of the mounting hub 18 in at least three rotational directions.

Figure 4A:
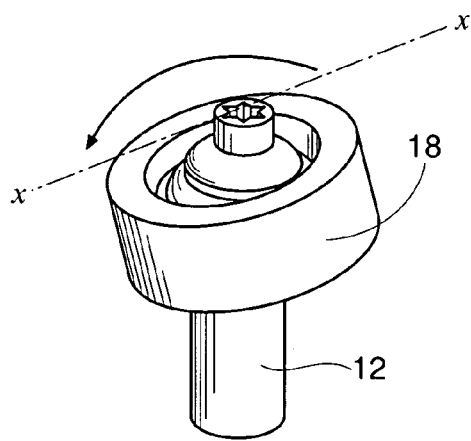
FIGS. 4a–4e illustrate rotational movement of the cooperating components of the assembled system shown in FIG. 2.
Figure 4B:
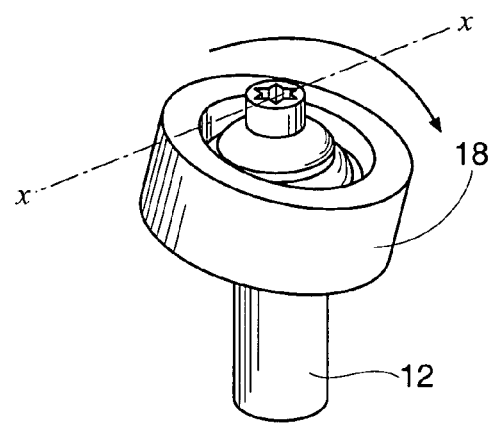

First, as represented by arrows in FIGS. 4a–4b, the mounting hub 18 can be rocked or rotated, i.e., tilted, about the x-axis (i.e., side to side rotation). This motion is permitted by the convex surfaces of the pivot pin 12, mounting hub 18, slip washer(s) 14, and lock washer(s) 16.

Figure 4C:
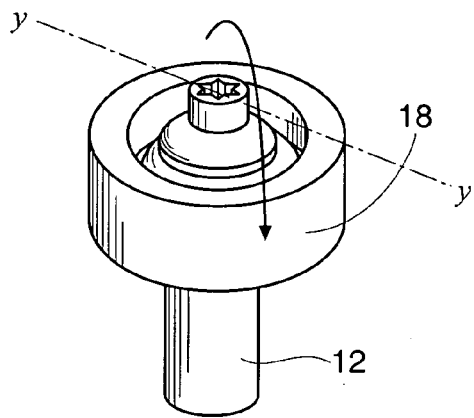
Figure 4D:
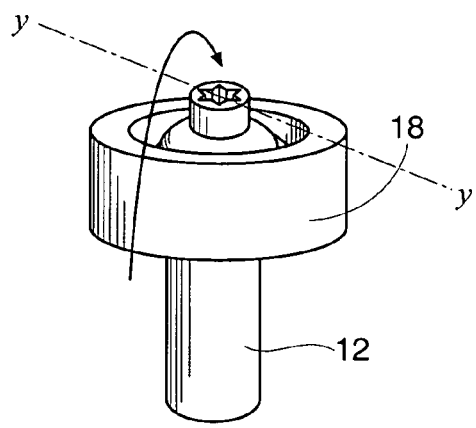

Second, as represented arrows in FIGS. 4c–4d, the mounting hub 18 can be rocked or rotated, i.e., tilted, about the y-axis (i.e., front to back rotation). This motion is permitted by the convex surfaces of the pivot pin 12, mounting hub 18, slip washer(s) 14, and lock washer(s) 16.

Figure 4E:
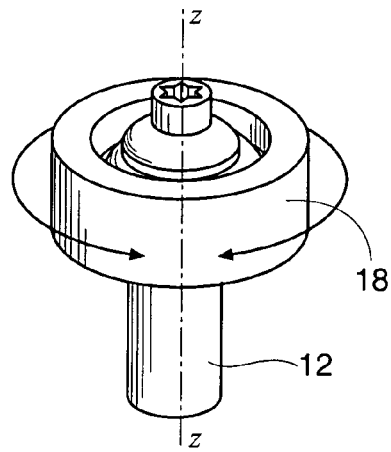

Third, as represented by arrows in FIG. 4e, the mounting hub 18 can be rotated 360° in either a clockwise or counterclockwise direction about the z-axis (i.e., axis of the pivot pin 12).

It is to be understood that the rotational and rocking movements permit adjustment in virtually an infinite number of rotational directions.

B. System 2:

Interior Hub Eccentrally Located with Respect to Mounting Surface

1. System Components

Figure 6:
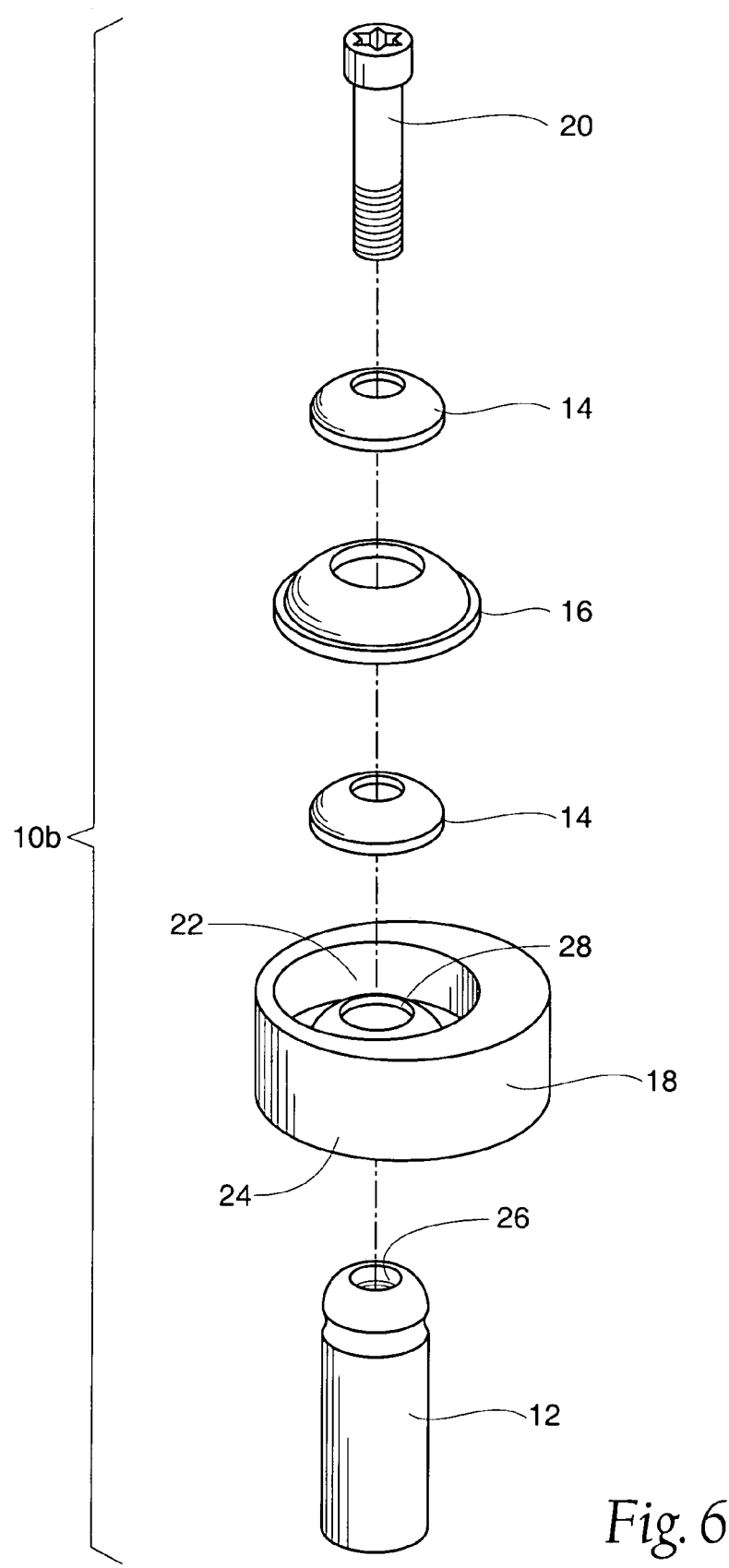
FIG. 6 is an exploded view of the components of an alternative embodiment of an adjustable locking mount system that embodies features of the invention, in which the mounting hub is eccentric.
Figure 7:
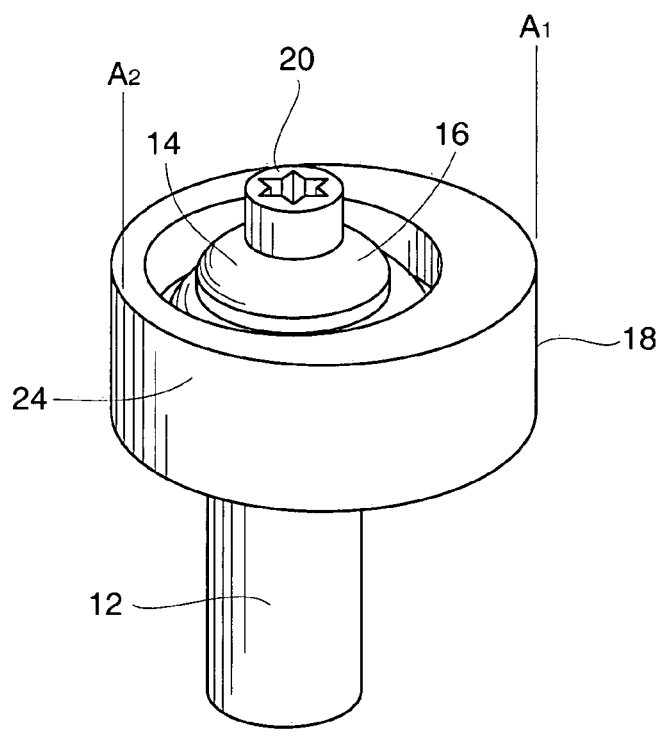
FIG. 7 is an assembled perspective view of the system shown in FIG. 6.
Figure 8:
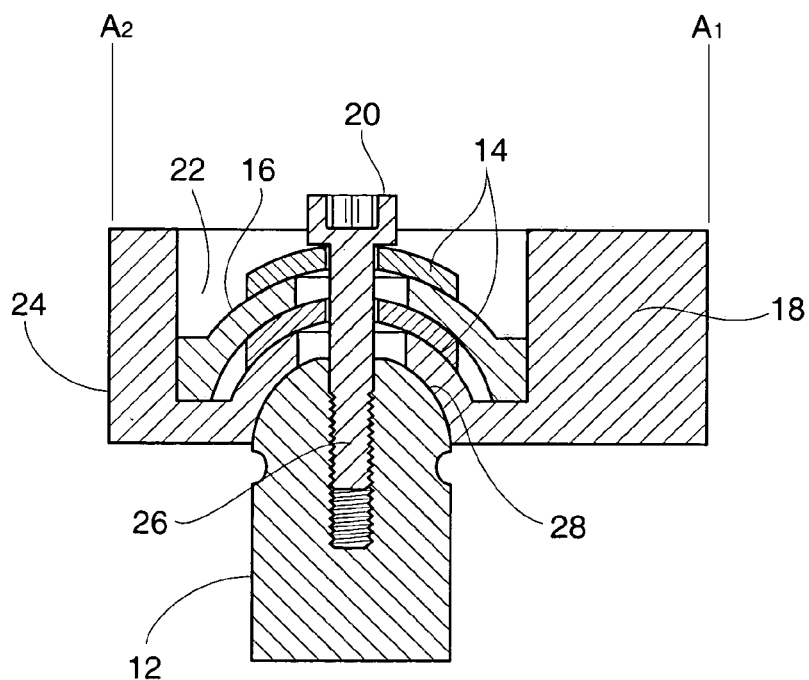
FIG. 8 is side sectional view of the assembled components of the system shown in FIG. 7.

FIG. 6 shows the individual components of an alternative system 10B providing an adjustable locking mount system. FIGS. 7 and 8 illustrate the system 10B when assembled.

Like system 10A, the system 10B comprises a pivot pin 12, at least one slip washer 14, at least one lock washer 16, a mounting hub 18, and a locking screw 20.

Also like system 10A, the mounting hub 18 has an exterior pivot surface 28 that is located centrally with respect to the interior hub 22. In this embodiment, as FIGS. 6–8 best show, the interior hub 22 is eccentric with respect to the mounting surface 24, such that the geometric center of the mounting hub 18 does not coincide with the center of rotation of the mounting hub 18 about the pivot pin 12. The eccentric configuration permits a broader range of adjustment.

2. Adjustment of the Orientation of the Mounting Hub

The system 10B as previously described enables the mounting hub 18 to be oriented in a variety of directions with respect to the pivot pin 12. The types of movement, and thus the types of adjustments permitted, will now be discussed.

The system 10B permits movement of the mounting hub 18 in at least five directions.

Figure 9A:
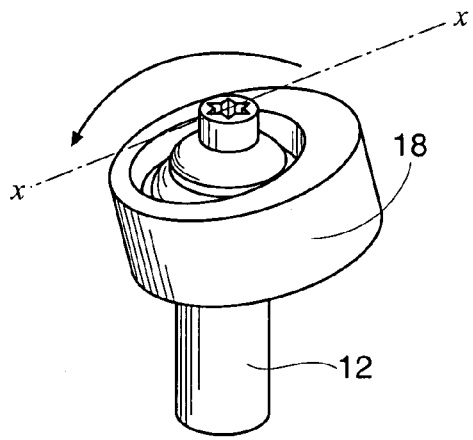
FIGS. 9a–9e illustrate rotational movement of the cooperating components of the assembled system shown in FIG. 7.
Figure 9B:
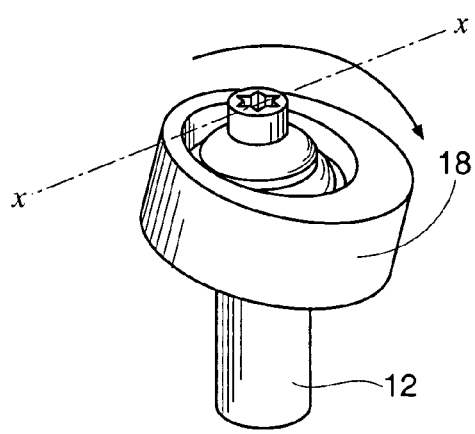

First, as represented by arrows in FIGS. 9a–9b, the mounting hub 18 can be rocked or rotated about the x-axis, as previously described for system 10A.

Figure 9C:
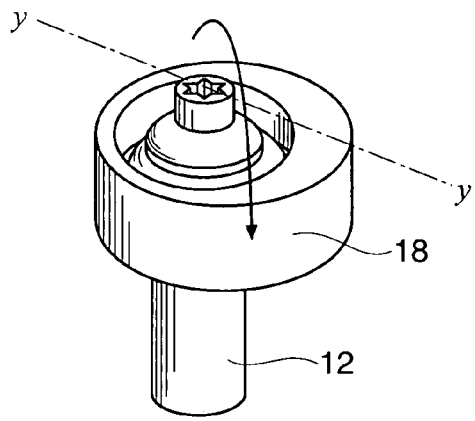
Figure 9D:
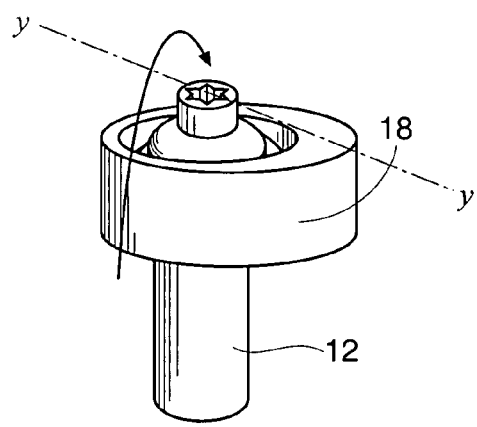

Second, as represented by arrows in FIGS. 9c–9d, the mounting hub 18 can be rocked or rotated about the y-axis, as also previously described for system 10A.

Figure 9E:
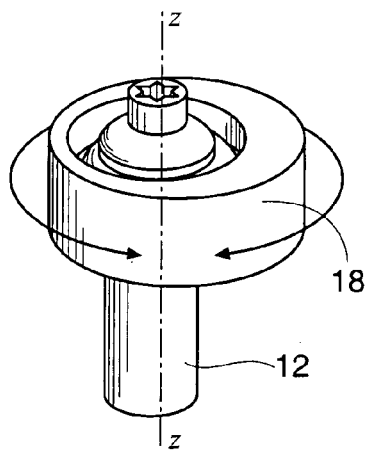

Third, as represented by arrows in FIG. 9e, the mounting hub 18 can be rotated up to 360° in either direction about the z-axis, as previously described for system 10A.

As best illustrated in FIGS. 7 and 8, when the mounting hub 18 includes an interior hub 22 that is eccentric relative to the mounting surface 24, the distance from the pivot pin 12 to the mounting surface 24 increases to a maximum value, depicted as point A1 and then decreases to a minimum value, depicted as point A2.

Reorientation or translation of the linear position of point A1 and point A2 with respect to the pivot pin 12 is possible when the mounting hub 18 is rotated about the z-axis.

Reorientation of points A1 and A2 with respect to the x-axis provides a fourth degree of freedom. Similarly, reorientation of points A1 and A2 with respect to the y-axis provides a fifth degree of freedom.

It is to be understood that the rotational and rocking movements just described permit adjustment in virtually an infinite number of directions.

After the desired position is obtained, the locking screw 20 is tightened to secure the mounting hub 18 in the desired position, as previously described for System 10A (see FIG. 5c).

II. Use of the System in Shoulder Replacement

FIGS. 10–23 detail the use of either of the previously-described systems 10A or 10B in shoulder replacement surgery. Desirably, system 10B would be employed, thereby providing the greatest range of adjustment. In the embodiment illustrated in FIGS. 10–23, the mount of system 10B is employed.

Figure 16:
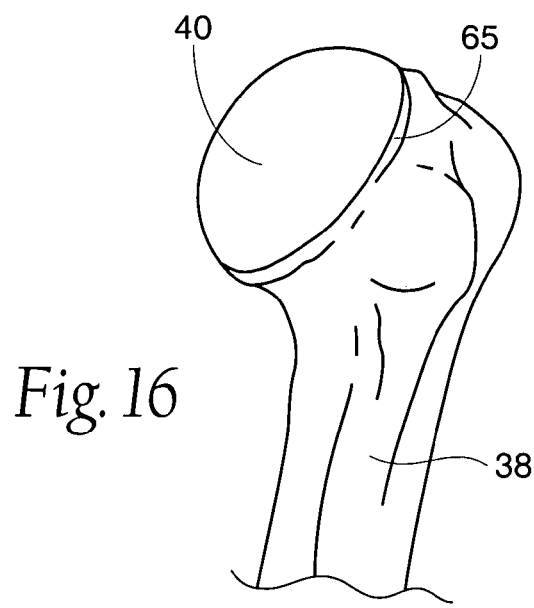
FIG. 16 is a perspective view of a humerus bone, with a line representing a cut in the ball portion of the humerus made during shoulder replacement surgery.

The long bone of the upper or proximal arm, as shown in FIG. 16, is known as the humerus 38. The proximal end of the humerus 38 comprises a ball-shaped head 40 that normally nests within the glenoid cavity of the shoulder bone, or scapula.

Through disease or injury, the head 40 of the humerus 38 can become damaged such that the shape of the head 40 is altered or the head 40 does not fit properly within the glenoid cavity. Such damage typically results in the shoulder joint becoming painful and a corresponding reduction in mobility of the joint.

Figure 10:
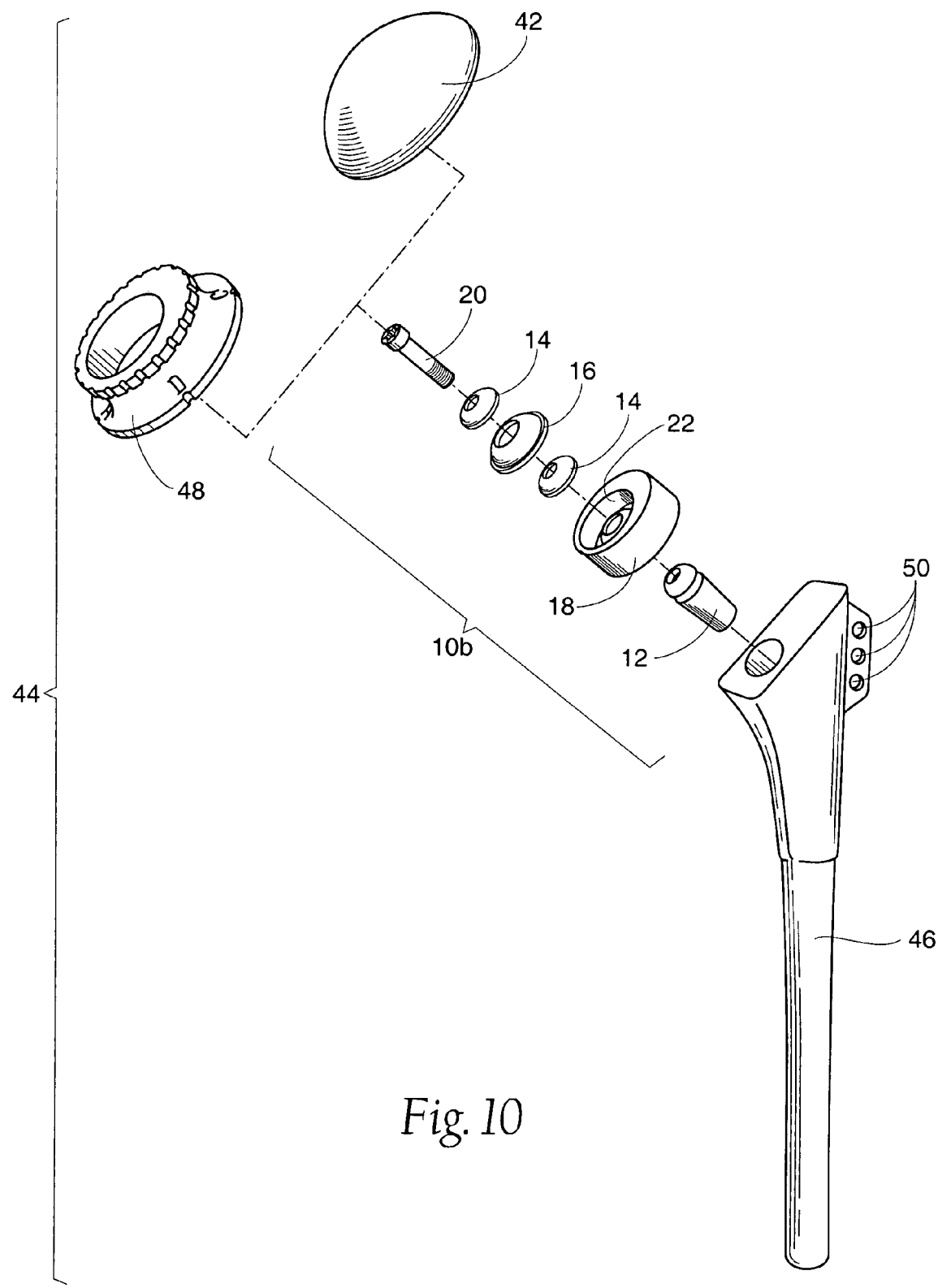
FIG. 10 is an exploded view of an adjustable locking mount system embodying features of the invention incorporated in a shoulder replacement assembly.

Conventional techniques provide for replacement of the head 40 of the humerus 38 with a prosthesis, or artifical head 42. As seen in FIG. 10, the system 10B, comprising a pivot pin 12, a mounting hub 18 (with eccentrically located interior hub 22), slip washers 14, a lock washer 16, and a locking screw 20, can be employed within a shoulder replacement assembly 44 suitable for implantation into a humerus 38. The system 10B would permit a physician to mount, position, and secure an artificial head 42.

Figure 11:
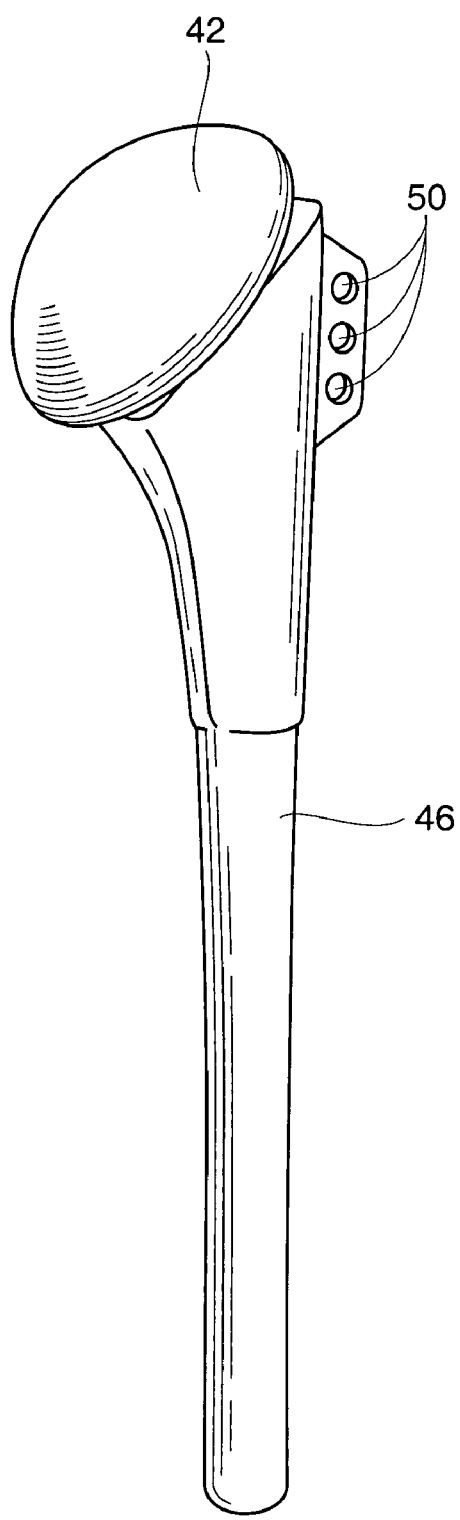
FIG. 11 is a perspective view of the assembled components of the system shown in FIG. 10.

As shown in FIG. 10, the replacement assembly comprises a stem 46 including tendon attachment holes 50, an assembled system 10B implanted within the stem 46, a trial ring 48, and an artificial head 42. FIG. 11 illustrates the replacement assembly 44 in assembled form.

The stem 46 is a conventional stem 46 suitable for implantation within a humerus 38. The stem 46 desirably includes tendon attachment holes 50 that serve to secure attachment of tendons (not shown) to the stem 46.

The stem 46 serves to hold the system 10B. That is, the pivot pin 12 is implanted within the stem 46 such that the convex portion protrudes at a pre-selected angle from the stem 46 (e.g., 35°).

The pivot pin 12 can be implanted within the stem 46 by various techniques. In one embodiment, the pin 12 is integrally molded with the stem 46. Alternatively, the pin 12 can be a separate member configured to mate with an existing stem 46. In a representative embodiment, the pin 12 includes a Morse taper, as seen in FIG. 10, configured to mate with a complementary tapered surface within the stem 46. In yet another embodiment, the pin 12 is configured to mate with the stem 46 by threaded engagement (not shown).

As also shown in FIG. 10, a trial ring 48 is desirably provided. The trial ring 48 is a rigid, generally ring-like member having an inner surface 52 and an outer surface 54. The inner surface 52 is desirably eccentric relative to the outer surface 54. The trial ring 48 can be made of plastic or any other suitable material.

The trial ring 48 is adapted to mate with the mounting hub 18, i.e., the trial ring's 48 inner surface 52 geometry approximates the geometry of the mounting surface 24. In the embodiment illustrated in FIG. 10, the mounting surface 24 is circular and conically tapered and the trial ring 48 has an inner surface 52 that is complementary circular and tapered.

Optionally, the inner surface 52 of the trial ring can be of a geometric or stepped formation adapted to mate with a complementary surface on the mounting surface 24, as previously described (not shown).

Figure 12A:
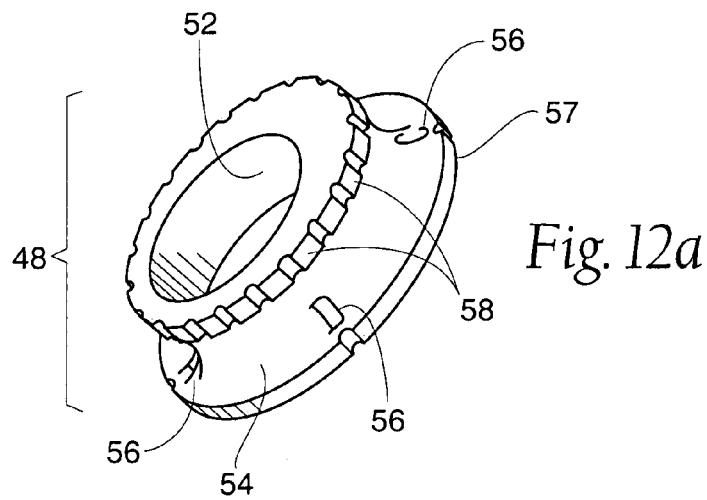
FIG. 12a is an enlarged perspective view of the top portion of the trial ring shown in FIG. 10.

As shown in FIG. 12a, the outer surface 54 of the trial ring 48 desirably has reference markers 56, e.g., A, B, C, and D, spaced circumferentially around the outer surface 54.

Optionally, as also seen in FIG. 12a, the outer surface 54 is tapered or radiused outward toward the bottom of the trial ring 48 for better visualization of the markers 56.

Figure 12B:
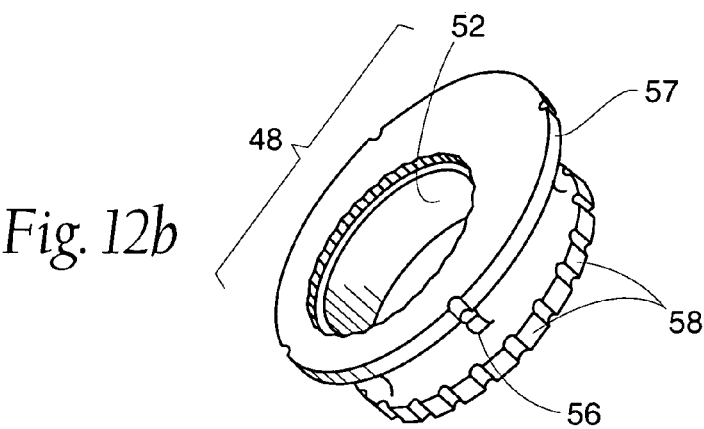
FIG. 12b is an enlarged perspective view of the bottom portion of the trial ring shown in FIG. 10.

In the embodiment illustrated in FIGS. 12a and 12b, the outer surface 54 of the trial ring 48 contains knurls 58. The knurls 58 provide for easier grasping of the trial ring 48. Optionally, the outer surface 54 does not contain knurls 58 or the outer surface 54 is otherwise adapted for grasping (not shown). The outside diameter 57 of the trial ring 48 corresponds or is equivalent to the outside diameter of the humeral head 42.

The trial ring 48 is adapted to engage the mounting hub 18 and pivot simultaneously with the mounting hub 18. In this arrangement, the reference markers 56 can be utilized for evaluation and recording of the desired position, as will be described in greater detail later.

As seen in FIG. 10, an artificial head 42 is also provided. The artificial head 42 is a rigid, dome-like member having interior 60 and exterior surfaces 62. The artificial head 42 can be made of stainless steel or other suitable materials.

Figure 13A:
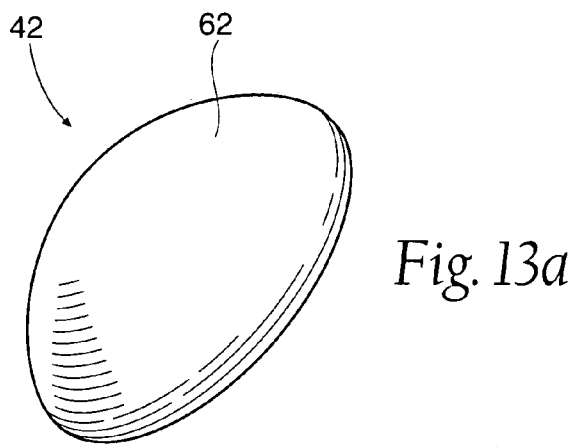
FIG. 13a is an enlarged perspective view of the top portion of the artificial head shown in FIG. 10.

As best illustrated in FIGS. 11 and 13a, the exterior surface 62 is domed to mimic the ball-like head 40 of the humerus 38.

Figure 13B:
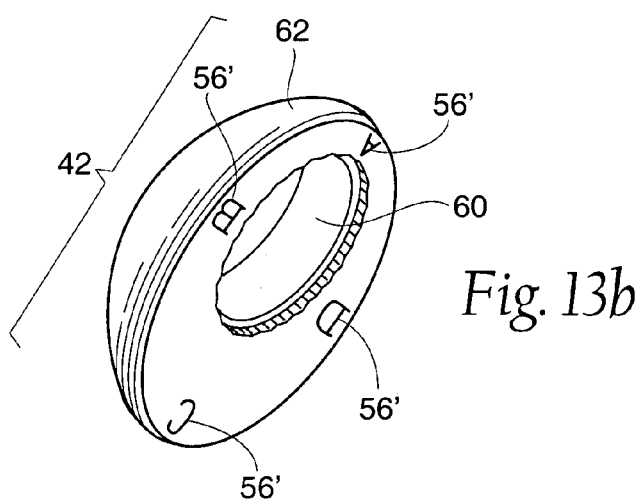
FIG. 13b is an enlarged perspective view of the bottom portion of the artificial head shown in FIG. 10, and further illustrating the interior surface of the artificial head.

As seen in FIG. 13b, the interior surface 60 is recessed and adapted to mate with the mounting surface 24. In the embodiment illustrated in FIG. 13b, the inner surface 60 is circular. Optionally, the interior surface 60 can be stepped to mate with a complementary mounting surface 24, as previously described (not shown).

As FIG. 13b also shows, the interior surface 60 desirably has reference markers 56' that are complementary to, i.e., mirror, the reference markers 56 on the trial ring 48. This assures that, when complementary markers 56 and 56' on the trial ring 48 and the artificial head 42 are similarly orientated with respect to the mounting hub 18, the position of the artificial head 42 will be the same as the position of the trial ring 48, as will be explained in greater detail later.

Desirably, as in the embodiment illustrated in FIG. 13b, the recessed inner surface 60 of the artificial head 42 is eccentrically located with respect to the outer surface 62.

When used in combination with the eccentrically located interior hub 22 of system 10B, this arrangement provides a "double-eccentric" system. The double-eccentric configuration provides a maximum range of adjustment from O axes offset to up to the maximum axes offset.

Figure 14A:
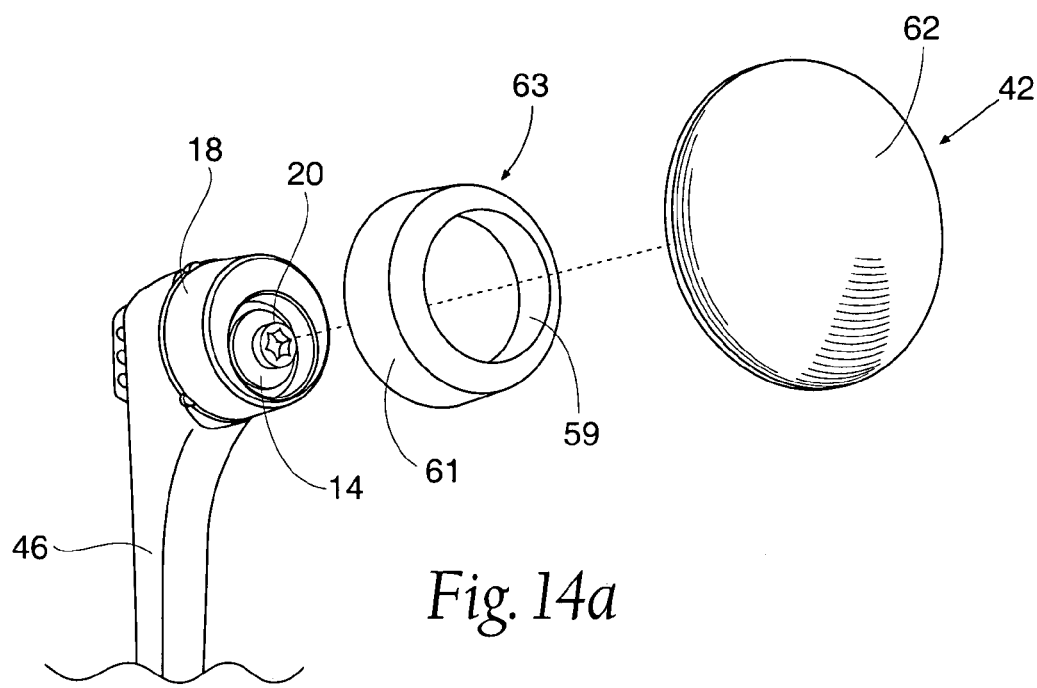
FIG. 14a is an exploded view of the components of an alternate embodiment of a shoulder replacement system embodying features of the invention and viewed from the head to the stem.
Figure 14B:
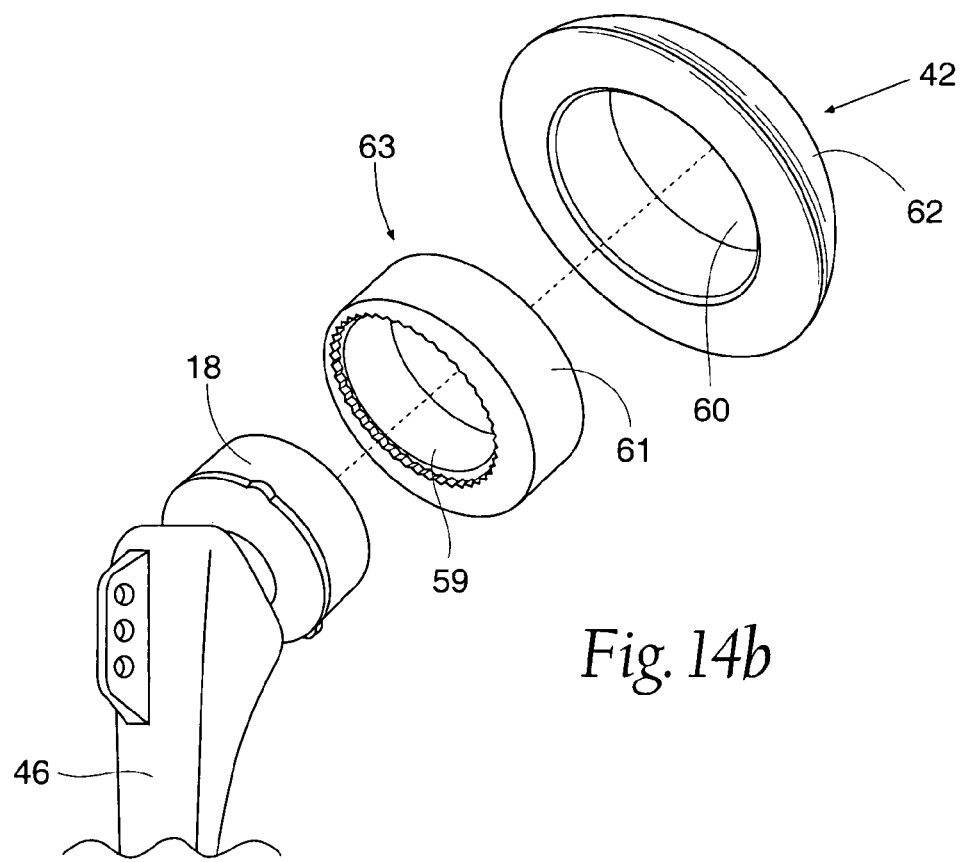
FIG. 14b is a view similar to FIG. 14a and viewed from the stem to the head.
Figure 15:
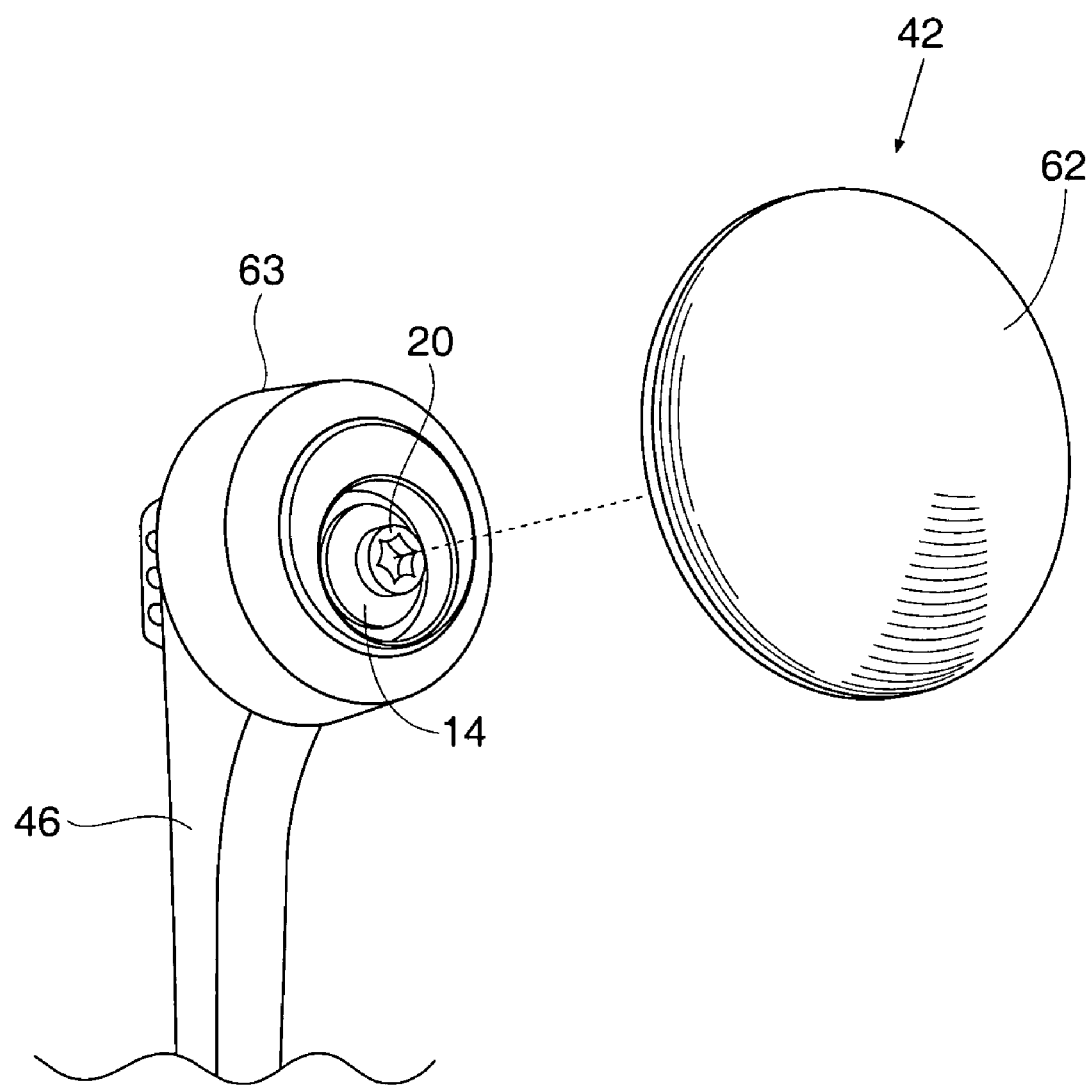
FIG. 15 is a view similar to FIGS. 14a and 14b and illustrating a partially assembled view of the system components.

In an alternate embodiment, shown in FIGS. 14a–14b and 15, the inner surface 60 of the artificial head 42 is centrally located with respect to the outer surface 62. In this arrangement, an intermediate collar 63 having an interior surface 59 and an exterior surface 61 can be provided.

The interior surface 59 of the collar 63 is eccentrically located with respect to the exterior surface 61 and configured to mate with the mounting surface 24. The exterior surface 61 is desirably configured to mate with the interior surface 60 of the artificial head 42. This arrangement also results in a double-eccentric configuration.

Figure 17:
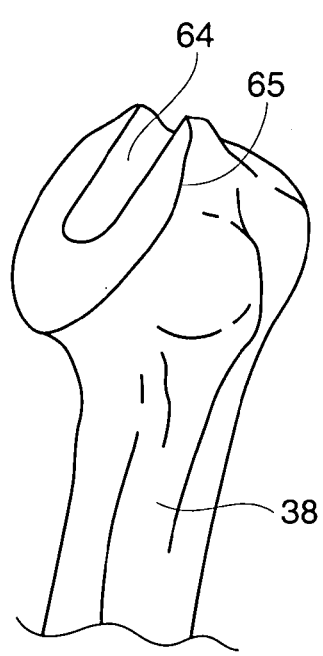
FIG. 17 illustrates a humerus as shown in FIG. 16, illustrating the head cut and removed from the humerus and a bore reamed into the bone.

In use, as seen in FIG. 16, the physician makes a cut 65 through the head 40 of the humerus 38 by conventional techniques. Next, as shown in FIG. 17, an interior bore 64 is reamed in the humerus 38 by conventional techniques to prepare the bone for receiving the stem 46.

Figure 18:
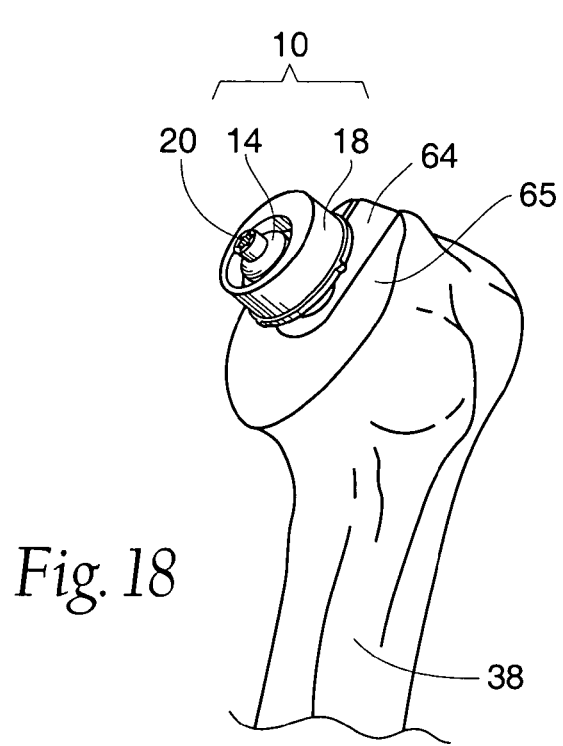
FIG. 18 is a perspective view illustrating a humerus as shown in FIG. 17, and further illustrating the insertion into the bore of a stem carrying an adjustable mount of the present invention.

The stem 46, incorporating the system 10B, is then inserted within the bore 64, as shown in FIG. 18. Tendons can then be attached to the stem 46 using the tendon attachment holes 50 (not shown).

Figure 19A:
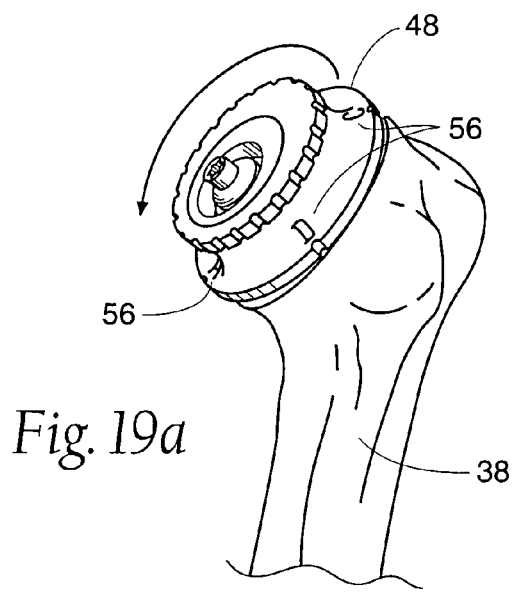
FIGS. 19a and 19b are perspective views illustrating a humerus as shown in FIG. 18, and further illustrating a trial ring engaging the mount and being rotated simultaneously with the mount.
Figure 19C:
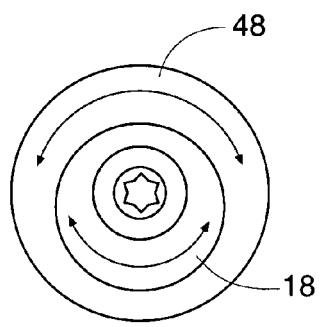
FIG. 19c illustrates the trial being and the mount rotated independently of each other.
Figure 19B:
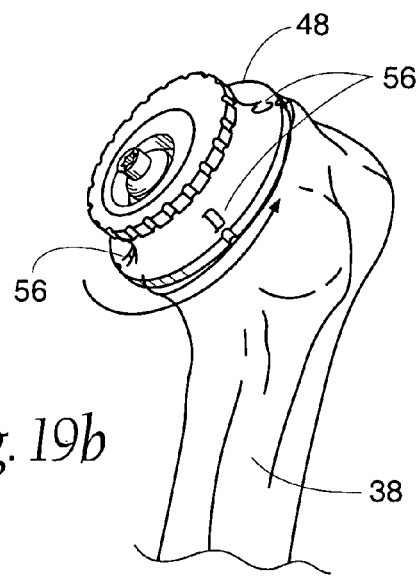

The trial ring 48 is then placed on the mounting hub 18. The eccentric interior hub 22 of the mounting hub 18, together with the eccentric inner surface of the trial ring 48 form a double-eccentric system, as shown in FIGS. 19a–19c. As represented by arrows in FIGS. 19a and 19b, the trial ring 48 is then rotated simultaneously with the mounting hub 18 until the desired position relative to the cut surface of the humerus 38 is achieved (e.g., center of trial ring 48 is centered with cut surface of humerus 38).

As FIG. 19c shows, the trial ring 48 is also adapted to rotate independently of the mounting hub 18.

Figure 20:
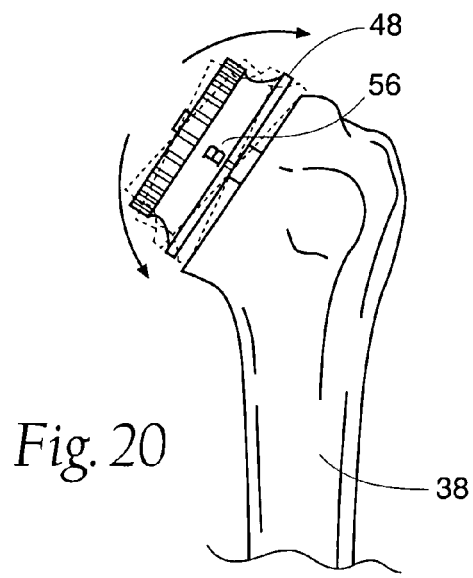
FIG. 20 illustrates a humerus as shown in FIGS. 19a and 19b, illustrating the trial ring being simultaneously tilted with the mount.

Then, as shown in FIG. 20, the trial ring 48 is tilted (represented by arrows and phantom lines in FIG. 20) with the mounting hub 18 until the desired position relative to the cut is achieved (e.g., parallel to cut).

Figure 21:
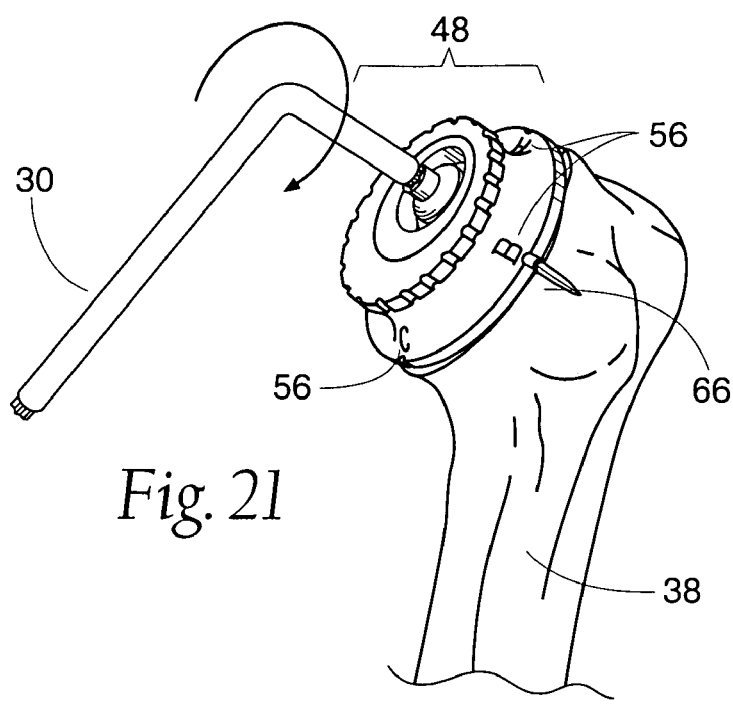
FIG. 21 illustrates a humerus as shown in FIG. 20, and further illustrates the procedure of locking the mount in a desired position.

As seen in FIG. 21, the mounting hub 18 is then secured in the desired position by tightening (represented by arrow in FIG. 21) the locking screw 20, e.g., with an Allen wrench 30.

As also seen in FIG. 21, the physician can then make a mark 66 on the humerus 38 corresponding to the position of a given reference marker 56 on the trial ring 48 when the mounting hub 18 is properly aligned.

For example, FIG. 21 illustrates a mark 66 made on the humerus 38 corresponding to the position of reference marker "B" when the trial ring 48 is properly aligned.

Figure 22:
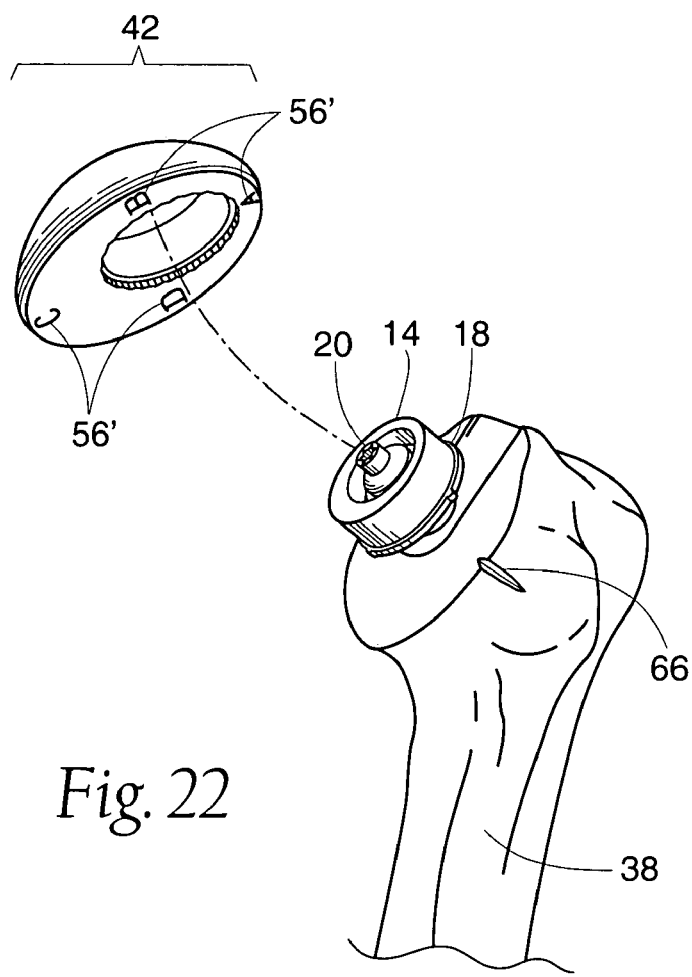
FIG. 22 shows a humerus as in FIG. 21, with the trial ring removed and illustrating the placement of an artificial head onto the mount.

Next, as illustrated in FIG. 22, the artificial head 42 is then orientated so that the desired reference marker on the interior surface 60 of the artificial head 42 is aligned with the mark 66 previously made on the humerus 38.

For example, FIG. 22 illustrates the reference marker "B" on the interior surface 60 of the artificial head 42 being aligned with the mark 66 previously made on the humerus 38.

The artificial head 42 is then placed (represented by phantom lines in FIG. 22) on the mounting hub 18 in this desired orientation.

Figure 23:
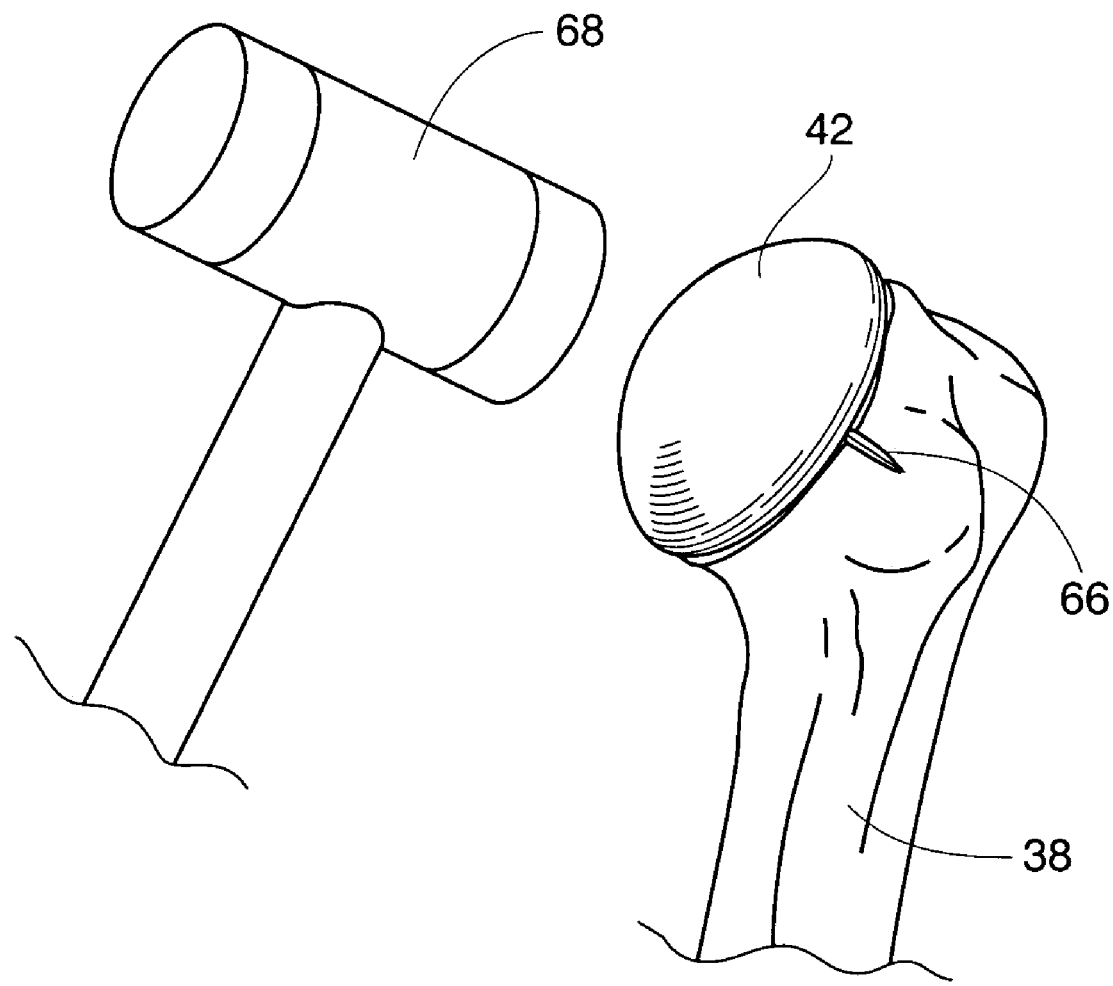
FIG. 23 illustrates a humerus as shown in FIG. 22, with the artificial head placed on the mount and further illustrating the use of a hammer to secure the artificial head on the mount.

Finally, as shown in FIG. 23, the physician seats and secures the aligned artificial head 42 in place by hitting the artificial head 42 with a hammer 68 to lock the tapers together before placing the artificial head 42 into position within the glenoid cavity.

III. Alternate Mounting Systems

A. Embodiment #1:

Eccentric Mechanism

Figure 24A:
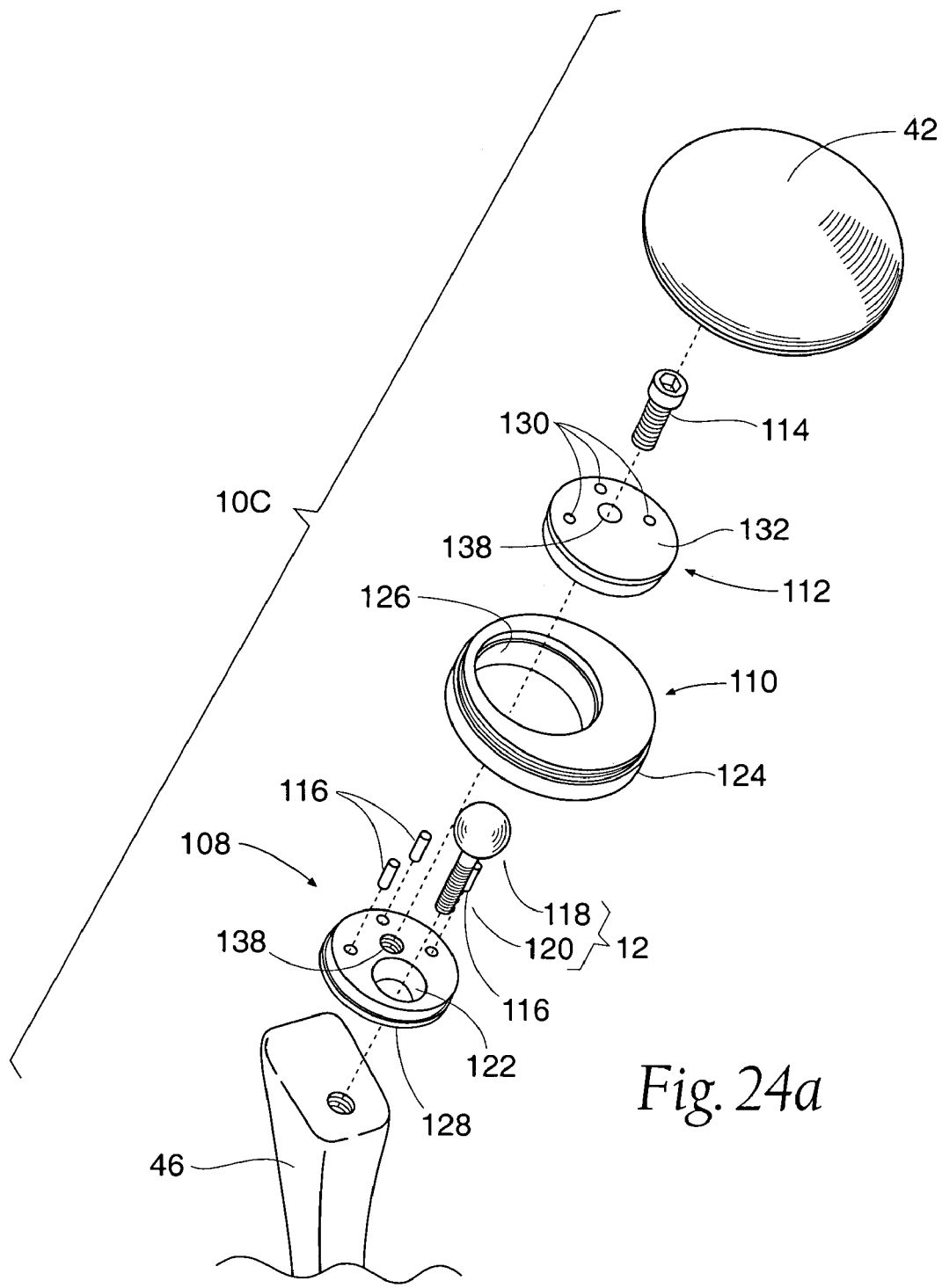
FIG. 24a is an exploded view of the components of an alternative embodiment of a shoulder replacement system embodying features of the invention and viewed from the head to the stem.

FIGS. 24a–29 detail an alternate embodiment of a shoulder prosthesis mounting system 10C embodying features of the invention. With reference to FIGS. 24a and 24b, the system 10C comprises a stem 46, a pivot pin 12, a bottom eccentric insert 108, an eccentric mount 110, a top eccentric insert 112, at least one fastener 114, at least one guidepin 116, and an artificial head 42.

The stem 46 is a conventional stem suitable for implantation into a humerus and serves to receive the pivot pin 12. The pivot pin 12 comprises a ball component 118 and a post component 120. The post 120 extends from the ball 118 and is sized to pass through the mount 110 and an eccentric opening 122 on the bottom insert 108 to mate with the stem 46, e.g., by threaded engagement (see e.g., FIG. 24a) or Morse taper (not shown).

In an alternate embodiment, the post 120 and the ball 118 are not integral. The post 120 is integral with the stem 46 and extends from the stem 46. The ball 118 is configured to mate with the post 120, e.g., by threaded engagement, and thus is selectively removable from the post 120.

In either embodiment, the stem 46 is configured to carry the post 120 such that the ball 118 protrudes at a pre-selected angle from the stem 46, e.g., 35°. Desirably, a portion of the post 120 remains exterior to the stem 46, enabling the mount 110 to pivot freely on the ball 118 (see FIG. 29).

The eccentric opening 122 is of a larger diameter than the post 120 and sized to permit rotation of the mount 110 about the x, y, and z axes, as will be described in greater detail later.

Figure 25:
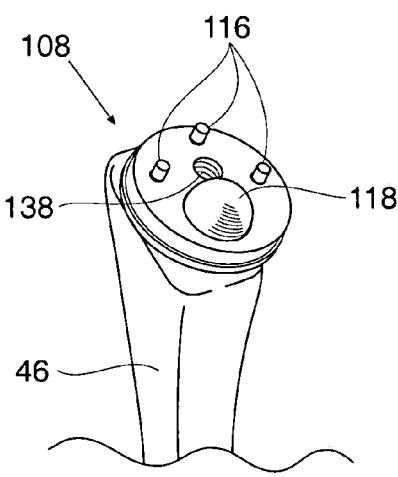
FIG. 25 is a view similar to FIGS. 24a and 24b and illustrating the use and placement of the pivot pin component of the system to secure the bottom insert component onto the stem component.

As seen in FIG. 25, the ball 118 is a spherical member sized to rest on the eccentric opening 122 of the bottom insert 108. This arrangement allows the ball 118 to serve as a pivot surface permitting adjustment of the eccentric mount 110.

Figure 24B:
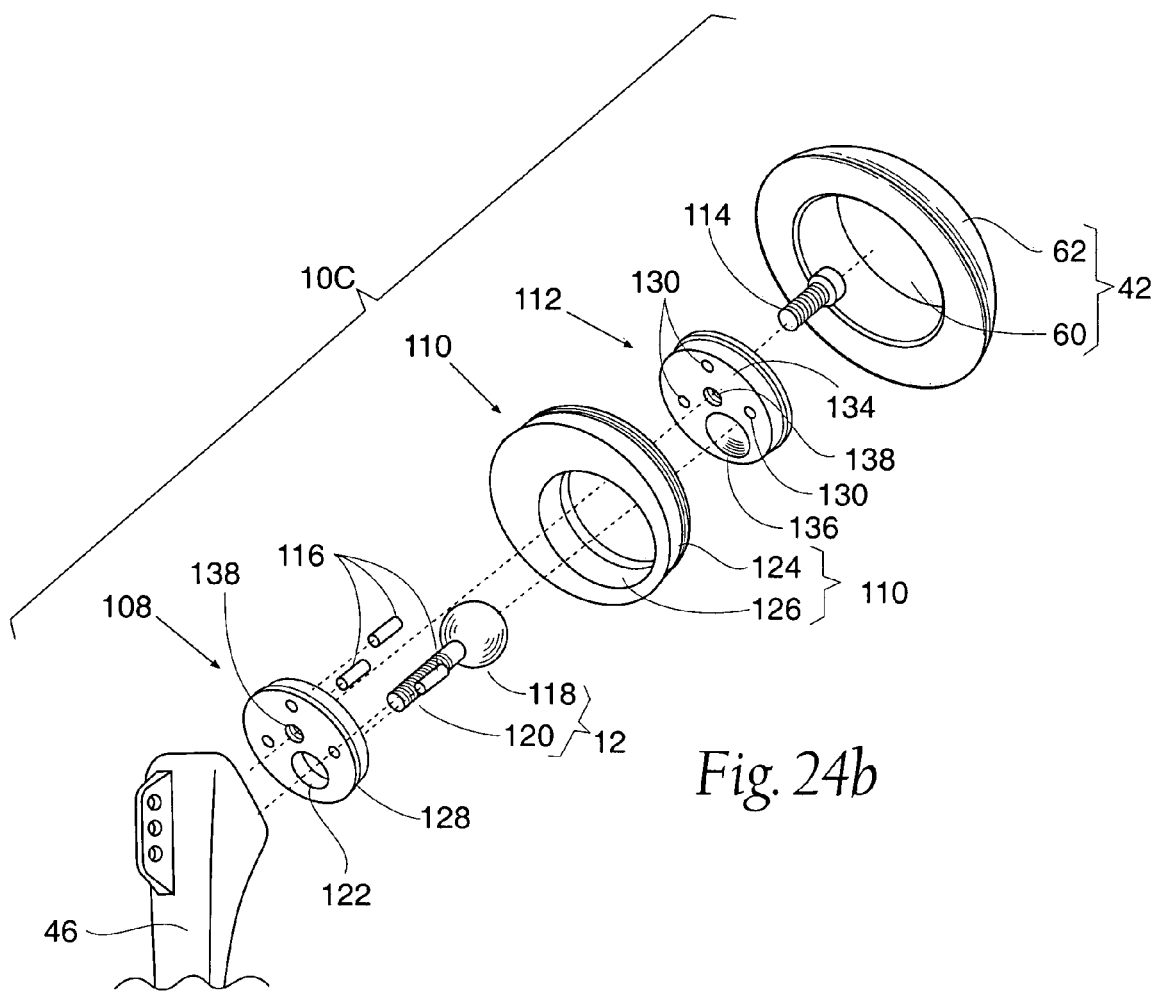
FIG. 24b is a view similar to FIG. 24a and viewed from the stem to the head.

The eccentric mount 110 is a ring-like member having an outer surface 124 and an inner surface 126, as seen in FIGS. 24a and 24b. As best illustrated in FIG. 24b, the inner surface 126 of the mount 110 is eccentric with respect to the outer surface 124. This arrangement allows the head 42 to be positioned eccentrally with respect to the mount 110. As FIGS. 25 and 26 show, the bottom insert 108 has an outer surface 128 adapted to mate with the inner surface 126 of the mount, e.g., by recessed slip fit that is free to rotate.

With reference again to FIG. 26, at least one guidepin 116 extends from the bottom insert 108. In the illustrated embodiment, three guidepins 116 are employed. The guidepins 116 are adapted to pass through complementary guidepin holes 130 on the top insert 112 when the top and bottom inserts 112 and 108 are properly aligned. Thus, the guidepins 116 serve to help align and secure the top and bottom inserts 112 and 108.

As best seen in FIG. 24b, the top eccentric insert 112 has a top surface 132 and a bottom surface 134. The bottom surface 134 has an eccentric recessed area 136 configured to mate with the ball 118. The top insert 112 is further adapted to rest on the bottom insert 108.

Figure 26:
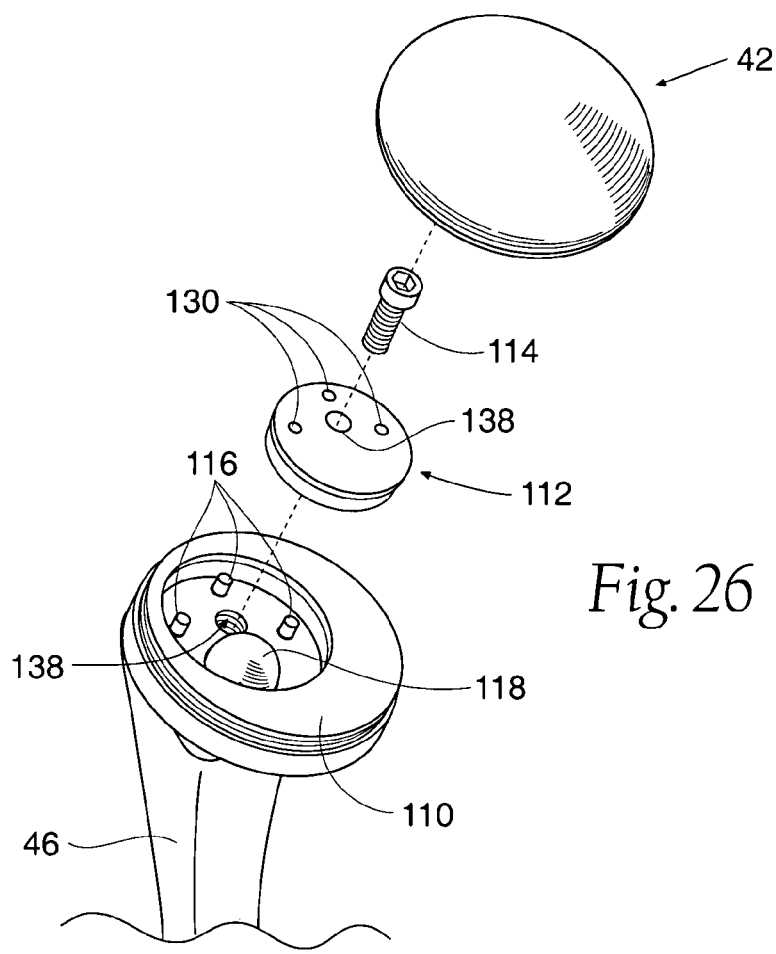
FIG. 26 is a view similar to FIG. 25 and illustrating the placement of the eccentric mount component onto the bottom insert component.
Figure 28:
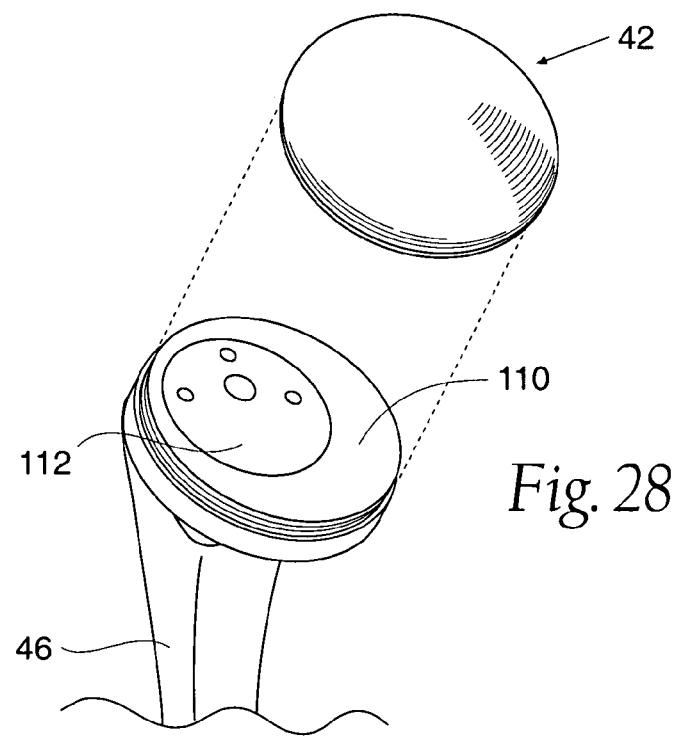
FIG. 28 is a partially assembled view of the system shown in FIGS. 24a and 24b and illustrating the placement of the top insert on the bottom insert.

As best shown in FIG. 26, the bottom and top inserts 112 and 108 each further comprise at least one fastener opening 138 adapted for passage of a fastener 114, e.g., a screw. The fastener 114, when tightened, serves to secure the mount 110 in a desired position by compressing the top and bottom inserts 112 and 108 together around the ball 118 and the mount 110. The "stacking" arrangement of the top and bottom inserts 112 and 108 serves to maximize the surface area compressed, thereby aiding in securing the mount 110 in a desired position.

The eccentric mount 110 along with the eccentric opening 122 of the bottom insert 108 and the eccentric recessed area 136 of the top insert 112 provide a double-eccentric system.

The artificial head 42 serves as a prosthesis for the head of a humerus, as previously described (see, e.g., FIG. 23). As FIG. 24b shows, the recessed interior surface 60 of the head 42 is desirably concentric with respect to the outer surface 62 and is threaded to mate with the outer surface 124 of the mount. Placement of the head 42 onto the mount 110 secures the head to the mount 110 (see FIG. 28).

The system 10C provides at least five degrees of freedom, thereby allowing a wide range of adjustment in multiple dimensions.

Figure 27A:
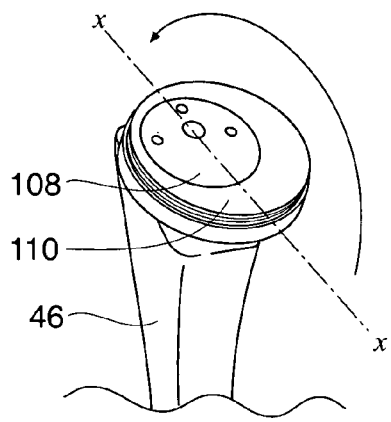
FIGS. 27a–27e are partially assembled views of the system shown in FIGS. 24a and 24b and illustrating rotational movement of the partially assembled system.
Figure 27B:
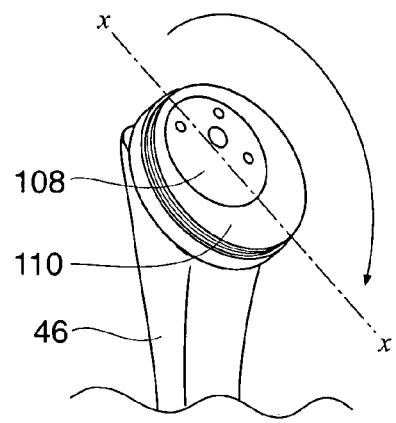

First, as illustrated by arrows in FIGS. 27a–27b, the mount 110 can be rocked or rotated, i.e., tilted, about the x-axis (i.e., side to side rotation).

Figure 27C:
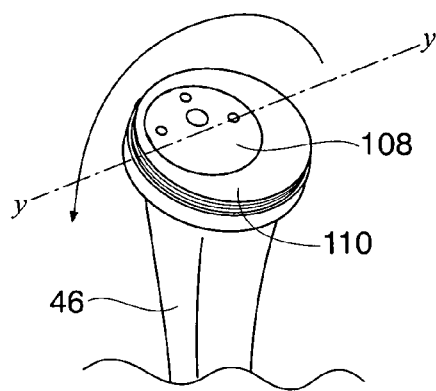
Figure 27D:
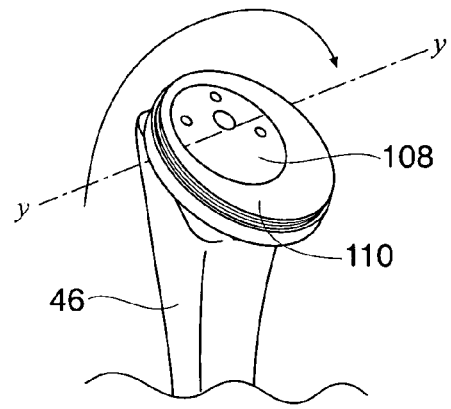

Second, as illustrated by arrows in FIGS. 27c–27d, the mount 110 can be rocked or rotated, i.e., tilted, about the y-axis (i.e., front to back rotation).

Figure 27E:
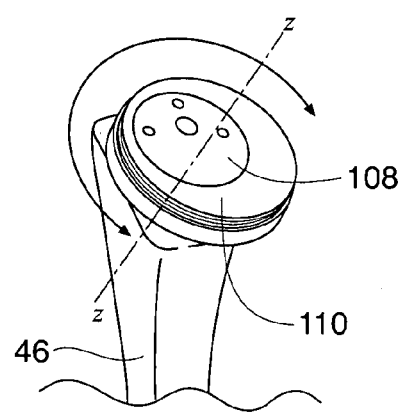
Figure 29:
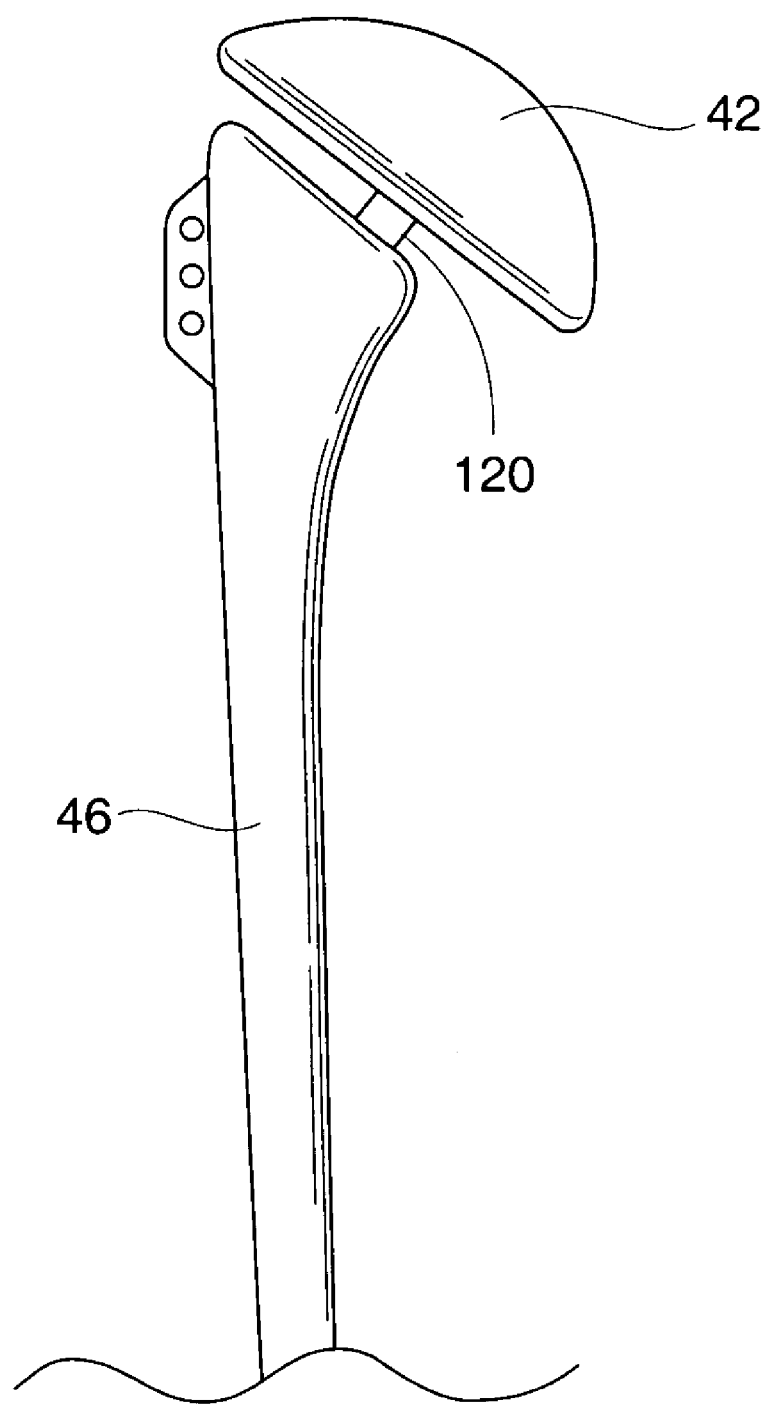
FIG. 29 is a perspective view of the components of the system shown in 24a and 24b assembled.

Third, as illustrated by arrows in FIG. 27e, the mount 110 can be rotated up to 360° in either direction about the z-axis.

Fourth and fifth, the double eccentric arrangement permits translation of the linear position of points A1 and A2 with respect to the pivot pin 12 when the inserts 108 and 112 and mount 110 are rotated, as previously described for system 10B (see FIGS. 7 and 8). This action permits translation along the x and y axes.

The double-eccentric configuration serves to maximize the range of translational adjustment possible under the fourth and fifth types of movement.

In use, as shown in FIG. 25, the pivot pin 12 is passed through the bottom insert 108 and the mount 110. The pivot pin 12 is then coupled to the stem 46, e.g., by screwing the post 120 into the stem 46. As FIG. 26 shows, the top insert 112 is then aligned with the bottom insert 108 by aligning the fastener openings 138 on the top and bottom inserts 112 and 108, the guidepins 116 with the guidepin holes 130, and the recessed area 136 with the ball 118.

The position of the mount 110 is then adjusted by rotating or rocking the mount about the x, y, and z axes (see FIGS. 27a–27e). The fastener 114 is then tightened to secure the mount 110 in a desired position (not shown). Finally, the head 42 is mounted onto the mount 110 (see FIGS. 28 and 29).

B. Embodiment #2:

Disk Slide Mechanism

Figure 30A:
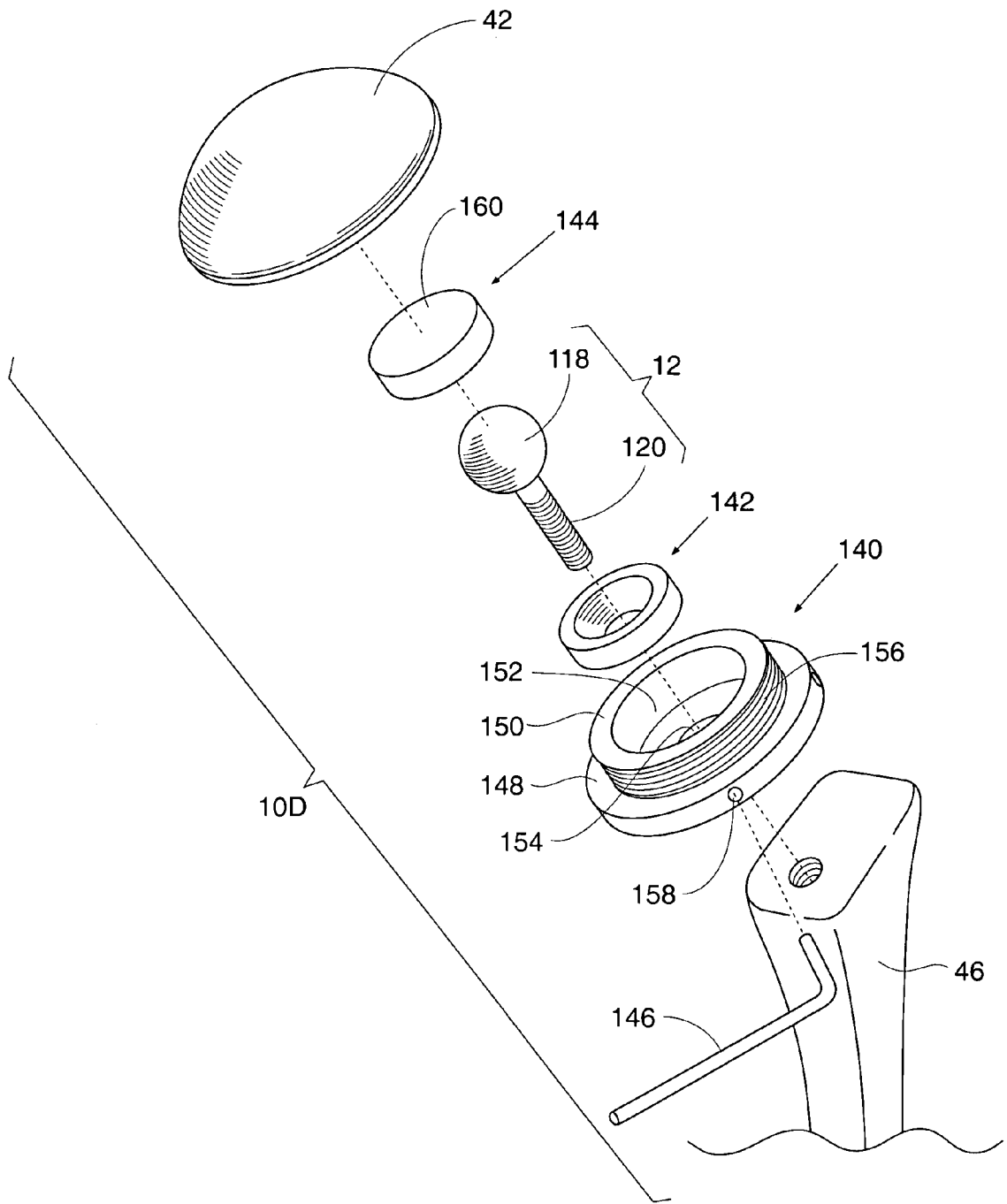
FIG. 30a is an exploded view of the components of an alternative embodiment of a shoulder replacement system embodying features of the invention and viewed from the head to the stem.

FIGS. 30a–34 detail another embodiment of a shoulder prosthesis mounting system 10D embodying features of the invention. With reference to FIGS. 30a and 30b, the system 10D comprises a stem 46, a pivot pin 12, a mounting ring 140, a bottom disk 142, a top disk 144, an artificial head 42, and a locking tool 146.

The stem is a conventional stem 46 and serves to receive a pivot pin 12, as previously described for system 10C The pivot pin 12 is similar in configuration to the pivot pin of System 10C. The post 120 is adapted to pass through the bottom disk 142 and the mounting ring 140 to mate with the stem 46, e.g., by threaded engagement.

Figure 31:
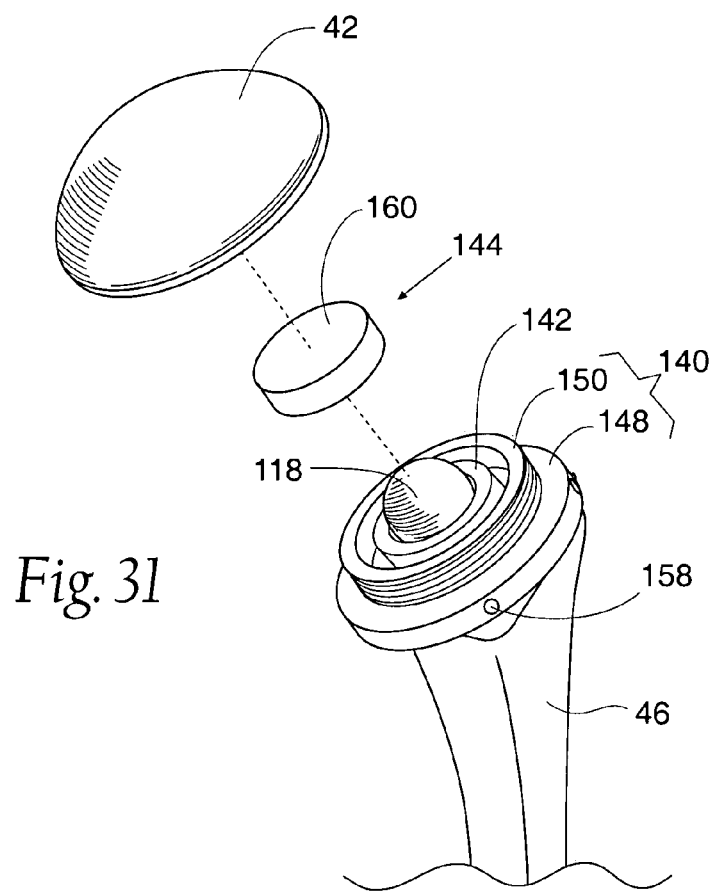
FIG. 31 is a view similar to FIGS. 30a and 30b illustrating the use of the pivot pin component to secure the mounting ring and the bottom disk to the stem.

As FIG. 31 shows, the ball 118 is sized to rest within the bottom disk 142. This arrangement allows the ball 118 to serve as a pivot surface, thereby permitting adjustment of the mounting ring 140.

As best seen in FIG. 30*a*, the mounting ring 140 is comprised of an outer ring 148 having a circular marginal surface and an integrally-formed upstanding inner annular ring 150. The center of the inner ring defines a chamber 152 and includes an opening 154 permitting passage of the post 120.

With reference again to FIG. 31, the chamber 152 is configured to receive the bottom disk 142 and the ball 118. The outer surface 156 of the inner ring 150 is desirably configured, e.g., threaded, to mate with the interior surface 60 of the head 42.

In the illustrated embodiment, the inner ring 150 is concentric with respect to the outer ring 148. However, the invention also contemplates embodiments in which the inner ring 150 is eccentric with respect to the outer ring 148.

Figure 34:
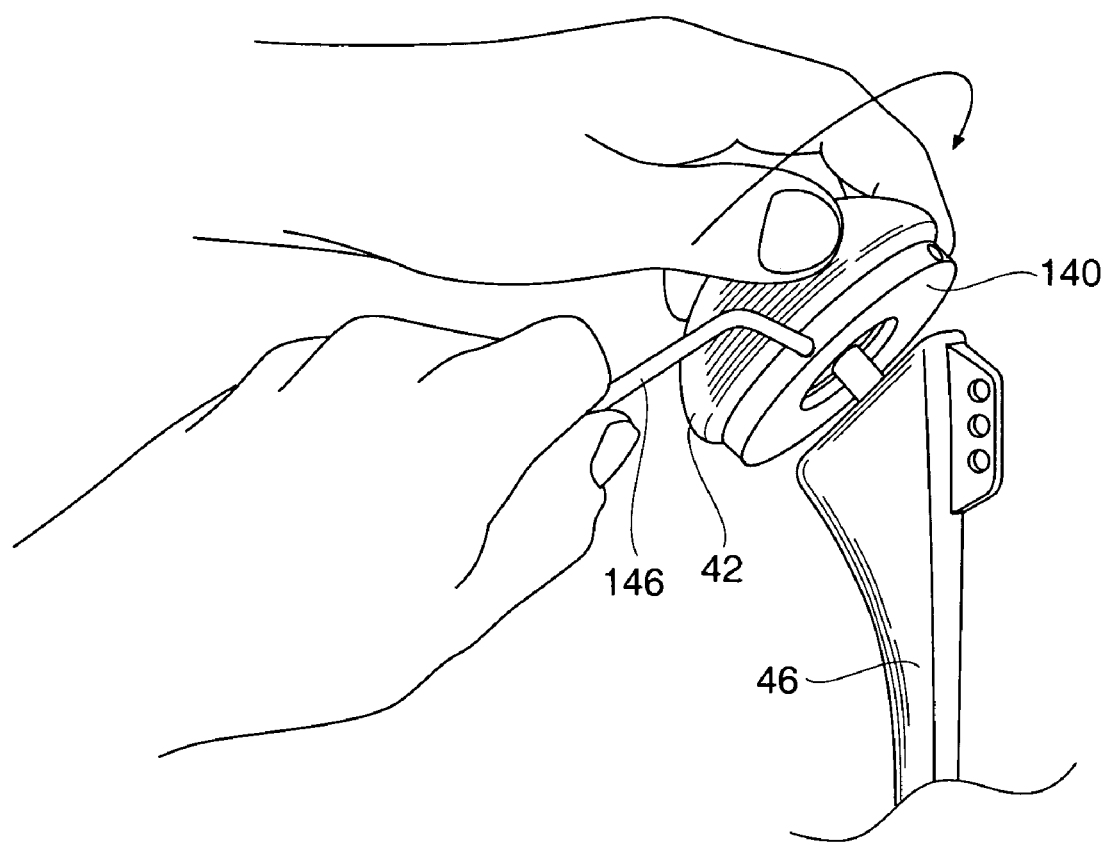
FIG. 34 is a view similar to FIGS. 33a–33e and illustrating the locking of the assembled system in a desired position.

As best seen in FIG. 34, the center opening 154 of the mounting ring 140 is of a larger diameter than the diameter of the post 120 and sized to permit translation of the mounting ring 140 about the x and y axes and rotation about the z-axis, as will be described in greater detail later.

As seen in FIG. 30*a*, the mounting ring 140 desirably has a locking aperature 158. The aperature 158 is a bore that transverses the circumferential margin of the mounting ring 140 and serves to receive the locking tool 146. The locking tool 146 is configured for insertion into the locking aperature 158 and allows rotation of the mounting ring 140 to tighten the head 42 onto the mounting ring 140 (see also FIG. 34).

Figure 32:
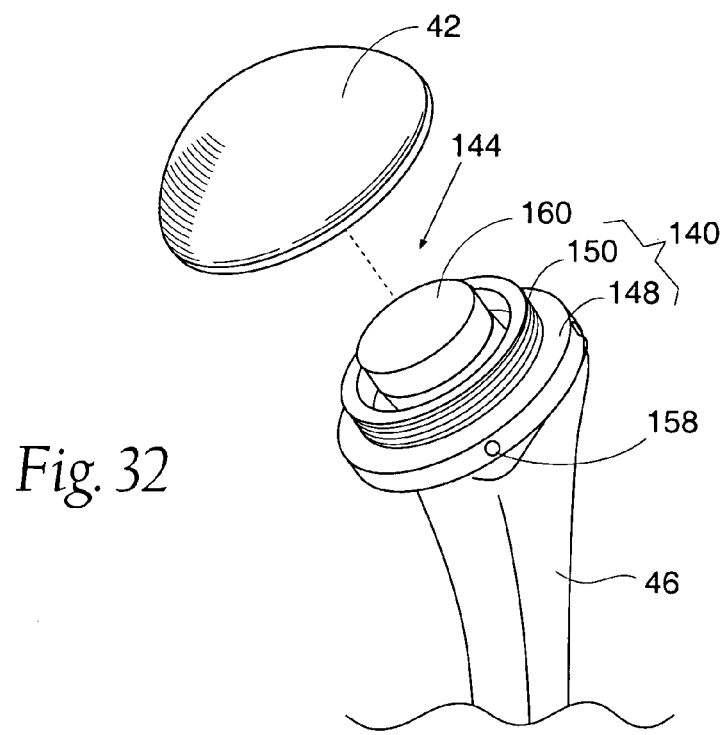
FIG. 32 is a view similar to FIG. 31 and illustrating the placement of the top disc on the bottom disk.

The bottom disk 142 is a ring-like member having an open center permitting passage of the post 120 and is configured to rest within the chamber 152 and receive the ball 118 (see FIGS. 30*a*–31). It is further configured to receive the top disk 144, as illustrated in FIG. 32.

Referring again to FIGS. 30*a* and 30*b*, the top disk 144 has a top surface 160 and a bottom surface 162. The top surface 160 is desirably flat or otherwise configured to permit compression of the top and bottom disks 144 and 142 upon mounting of the head 42 onto the mounting ring 140. The bottom surface 162 has a recessed area 164 configured to mate with the ball 118. The top disk 144 is further configured to rest on the bottom disk 142 (see also FIG. 32).

This stacking arrangement permits compression of the top and bottom disks 144 and 142 as the head 42 is mounted onto the mounting ring 140 and serves to maximize the surface area compressed, thereby securing the mounting ring 140 in a desired position.

Figure 30B:
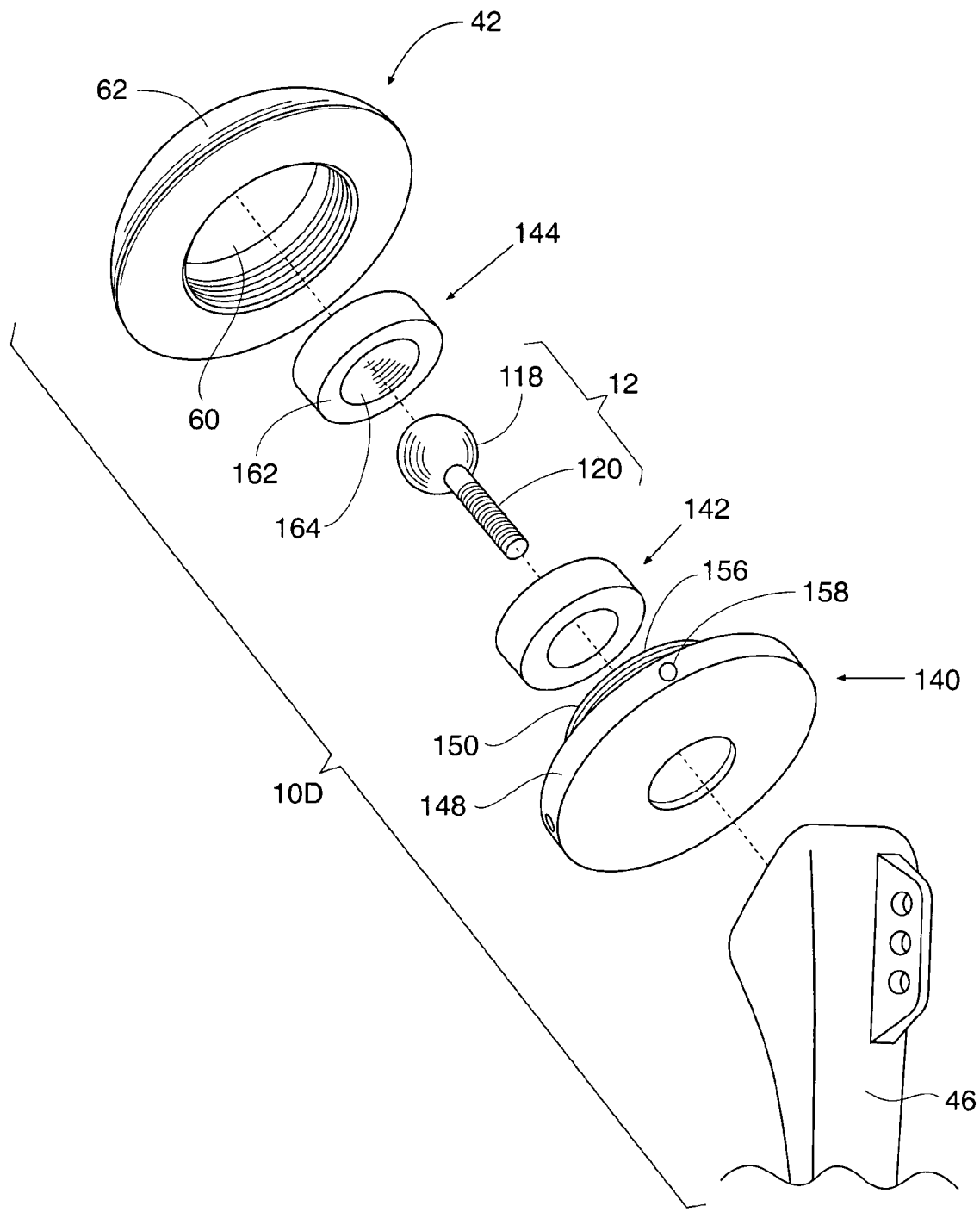
FIG. 30b is view similar to FIG. 30a and viewed from the stem to the head.

The artificial head 42 serves as a prosthesis for the head of a humerus, as previously described. As seen in FIG. 30*b*, the recessed interior surface 60 of the head 42 is desirably concentric with respect to the outer surface 62 of the head 42. The invention also contemplates, however, embodiments in which the interior surface 60 is eccentric. The interior surface 60 of the head 42 is also desirably threaded or otherwise configured to mate with the inner ring 150 of the mounting ring 140.

Similar to system 10C, the system 10D provides at least five degrees of freedom.

Figure 33A:
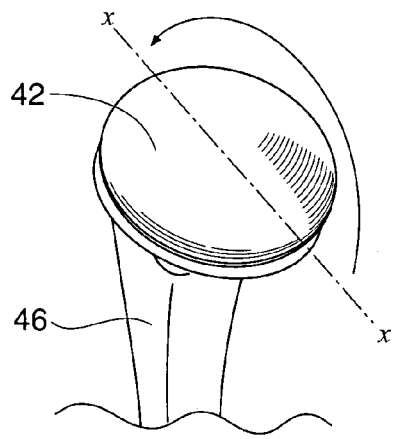
FIGS. 33a–33e are views similar to FIG. 32 and illustrating the placement of the head component onto the mounting ring component and further illustrating the rotational movement of the assembled system.
Figure 33B:
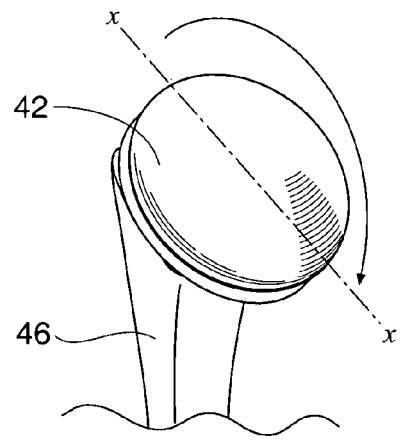

First, as illustrated by arrows in FIGS. 33*a*–33*b*, the mounting ring 140 can be rocked or rotated, i.e., tilted, about the x-axis (i.e., side to side rotation).

Figure 33C:
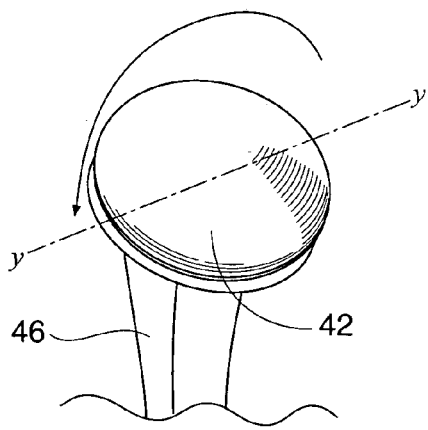
Figure 33D:
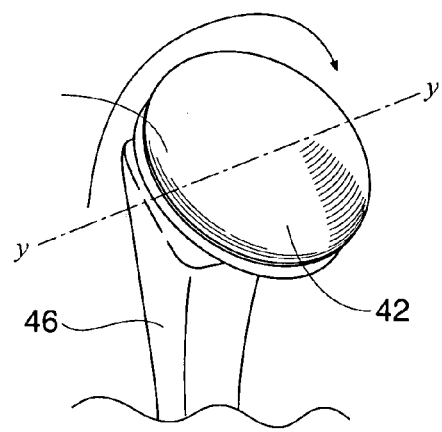

Second, as illustrated by arrows in FIGS. 33*c*–33*d*, the mounting ring 140 can be rocked or rotated, i.e., tilted, about the y-axis (i.e., front to back rotation).

Figure 33E:
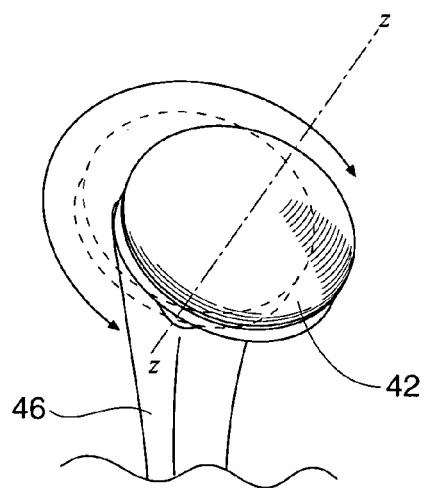

Third, as illustrated by arrows in FIG. 33*e*, the mounting ring 140 can be rotated up to 360° in either direction about the z-axis.

The difference between the outside diameter of the top and bottom disks 144 and 142 and the inside diameter of recessed chamber 152 forms a gap, as seen in FIG. 32. This arrangement permits linear translation along the x-axis, providing a fourth degree of freedom, and the y-axis, providing a fifth degree of freedom.

In use, with reference to FIGS. 30*a*–32, the post 120 is passed through the bottom disk 142 and the mounting ring 140. The post 120 is then coupled to the stem 46, e.g., by screwing. The top disk 144 is then aligned with the bottom disk 142 by aligning the recessed area 164 with the ball. Next, the head 42 is mounted onto the mounting ring 140.

The position of the head 42 is then adjusted by rotating and rocking the head 42 about the x, y, and z axes (see FIGS. 33*a*–33*e*). As FIG. 34 illustrates, the locking tool 146 is then inserted into the locking aperture 158. As represented by arrows in FIG. 34, the mounting ring 140 is then rotated by use of the locking tool 146 to tighten the head 42 onto the mounting ring 140. This action places all the components in compression and fixes the head 42 in place.

C. Embodiment #3:

Slotted Mechanism

Figure 35A:
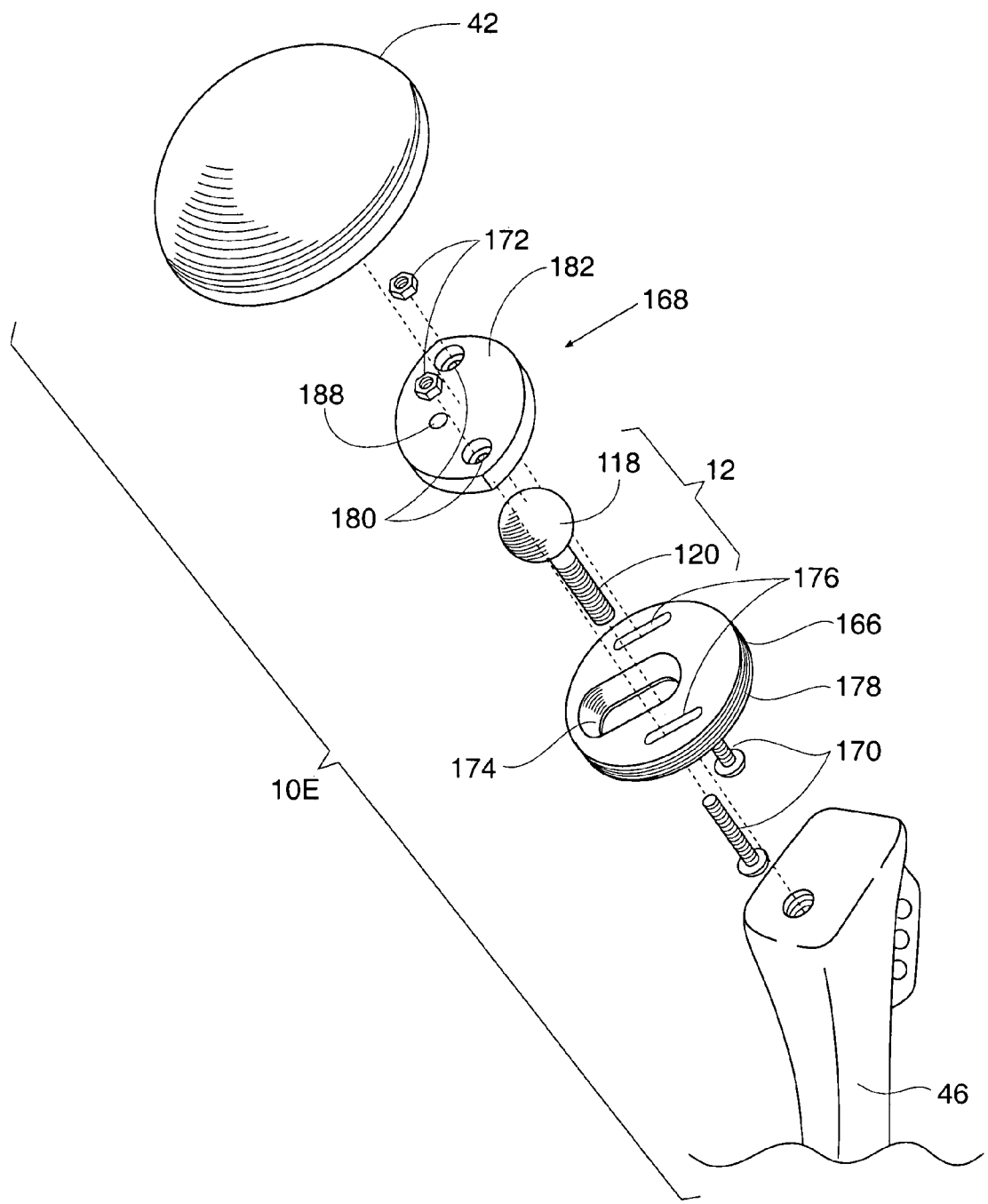
FIG. 35a is an exploded view of an alternative embodiment of a shoulder replacement system embodying features of the invention viewed from the head to the stem.

FIGS. 35*a*–40 detail another embodiment of a shoulder prosthesis mounting system 10E embodying features of the invention. With reference to FIGS. 35*a* and 35*b*, the system comprises a stem 46, a pivot pin 12), a bottom plate 166, a top plate 168, at least one fastener 170, and at least one fastening element 172 for securing the fastener 170.

The stem 46 and pivot pin 12 are configured as previously described for systems 10C and 10D. The post 120 is adapted to pass through the bottom plate 166 to mate with the stem 46, e.g., by threaded engagement. The ball 118 is sized to rest on the bottom plate 166. This arrangement allows the ball 118 to serve as a pivot surface that permits adjustment of the bottom plate 166.

Figure 36:
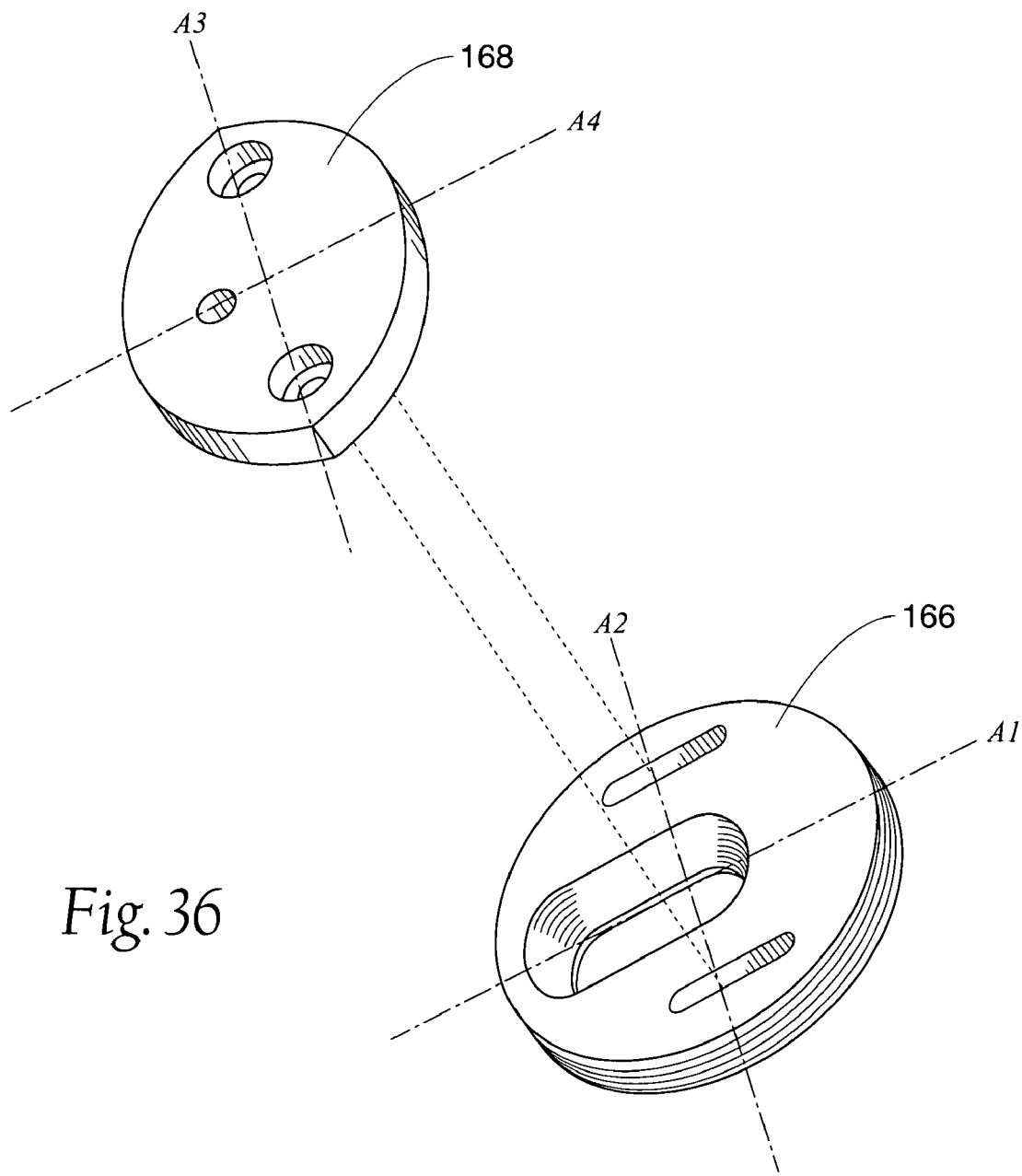
FIG. 36 is an exploded view of the bottom and top plate components of the system shown in FIGS. 35a and 35b and illustrating the major and minor axes of the top and bottom plates.

As shown in FIG. 36, the bottom plate 166 is a circular member having a major axis A1 and a minor axis A2. An elongated eccentric slot 174 is provided along the major axis A1. The bottom plate 166 also provides a pair of elongated fixation slots 176 radially spaced from the center and parallel to the major axis A1. The fixation slots 176 allow the position of the top plate 168 to be laterally adjusted with respect to the bottom plate 166. The fixation slots 176 also serve to receive fasteners 170, e.g., bolts, to secure the position of the top plate 168.

Figure 37:
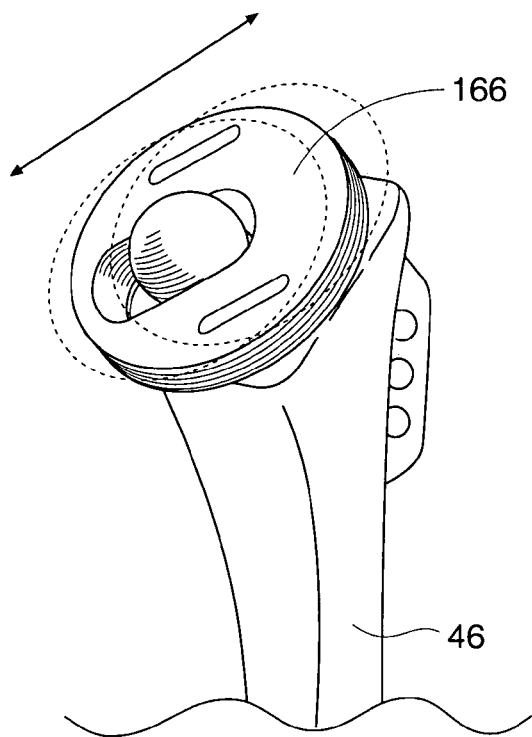
FIG. 37 is a partially assembled view of the system shown in FIGS. 35a and 35b and illustrating the use of the pivot pin to secure the placement of the bottom plate onto to stem.

As shown in FIG. 37, the eccentric slot 174 receives the ball 118 and allows lateral, i.e., side to side, adjustment (represented by arrows and phantom lines in FIG. 37) of the position of the ball 118 within the eccentric slot 174.

Figure 35B:
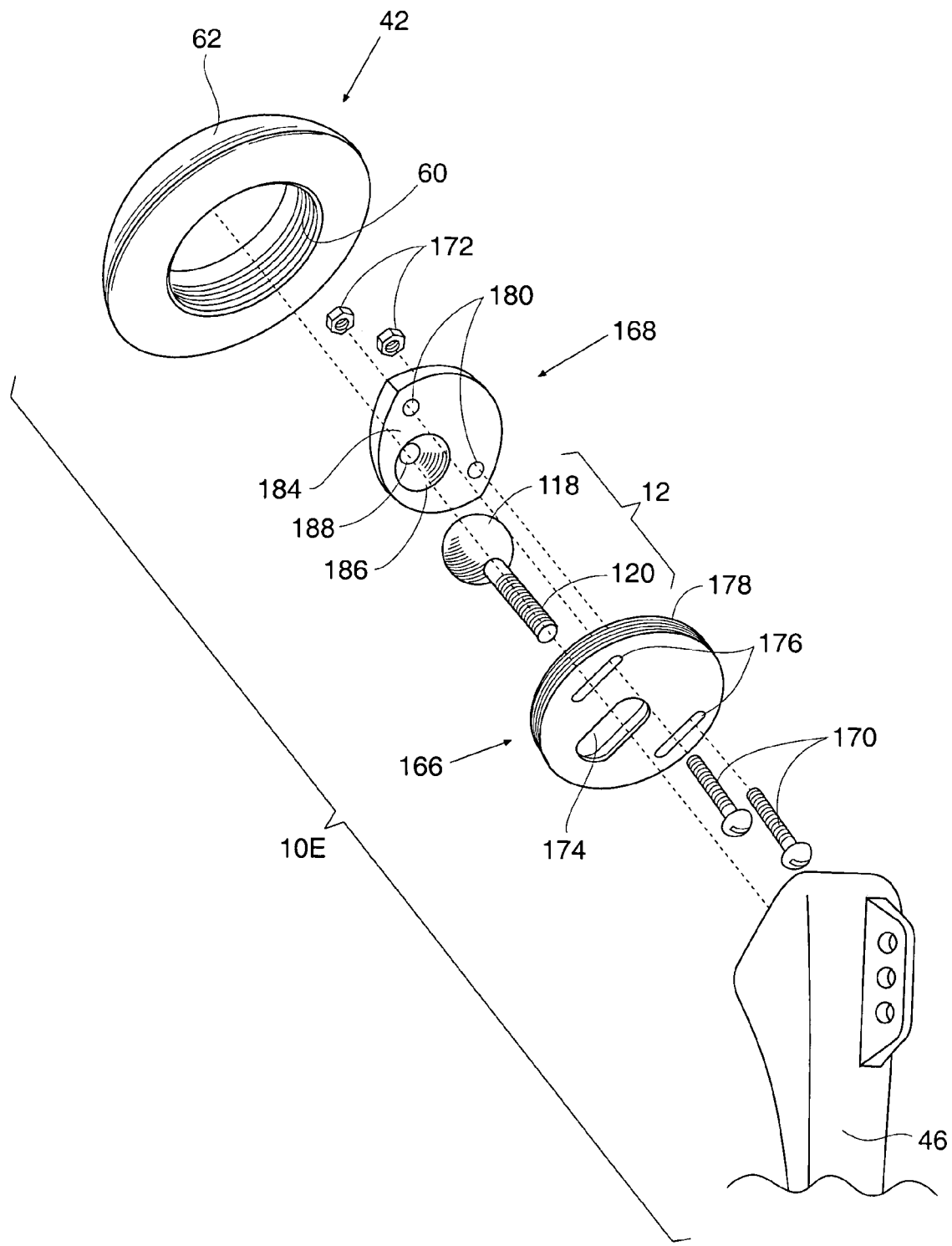
FIG. 35b is a view similar to FIG. 35a and viewed from the stem to the head.

The bottom plate 166 includes a circumferential outer surface 178 configured to mate with the head 42, e.g., by threaded engagement (see e.g., FIG. 35*b*). The bottom plate 166 serves to receive the top plate 168 in a stacked configuration.

Referring again to FIG. 36, the top plate 168 is a generally elliptical member having a major axis A3 and a minor axis A4. The major axis A3 parallels the minor axis A2 of the bottom plate 166 and the minor axis A4 parallels the major axis A1 of the bottom plate 166 when the top plate 168 is aligned with bottom plate 166. The top plate 168 further provides fastener receiving openings 180 sized and configured to receive the fasteners 170.

The top plate 168 further provides a top surface 182 and a bottom surface 184. The top surface 182 is configured to receive a fastening element 172 for the fastener 170, e.g., a nut. The bottom surface 184 includes a recessed area 186 configured to mate with the ball 118. The recessed area 186 desirably includes an opening 188 adapted for viewing the ball 118, thereby aiding in aligning the top plate 168 with respect to the bottom plate 166. The top plate 168 is further configured to rest on the ball 118, leaving a gap between the top plate 168 and bottom plate 166.

The fasteners 170, when tightened, serve to secure the plates 166 and 168 to the ball 118 in a desired position by compressing the top and bottom plates 166 and 168 together. The stacked arrangement of the plates 166 and 168 serves to maximize the surface area compressed, thereby aiding in securing the plates 166 and 168 in the desired position relative to the ball 118.

The artificial head 42 serves as a prosthesis for the head of a humerus, as previously described. The recessed interior surface 60 of the head 42 is desirably concentric with respect to the exterior surface 62 of the head 42, as shown in FIG. 35b. It should be understood, however, that the invention also contemplates embodiments in which the interior surface 60 is eccentric.

Similar to systems 10C and 10D, the system 10E provides at least five degrees of freedom.

Figure 39A:
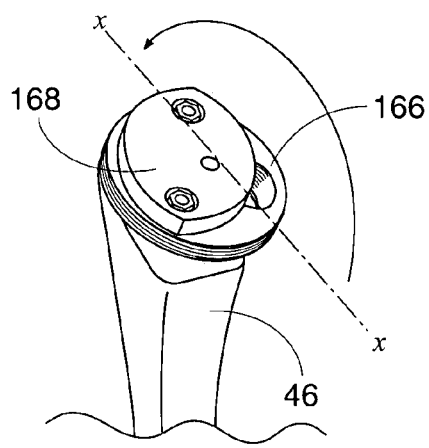
FIGS. 39a–39e are views similar to FIG. 38 and illustrating rotational movement of the partially assembled system.
Figure 39B:
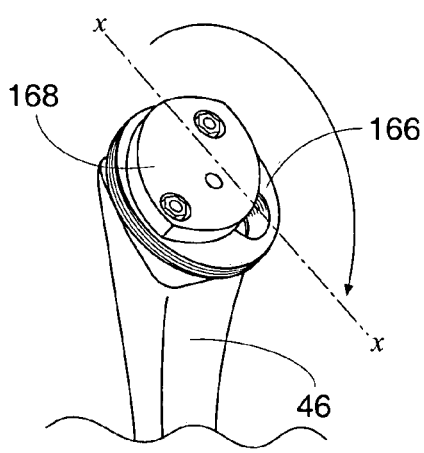

First, as illustrated by arrows in FIGS. 39a–39b, the bottom plate 166 can be rocked or rotated, i.e., tilted, about the x-axis (i.e., side to side rotation).

Figure 39C:
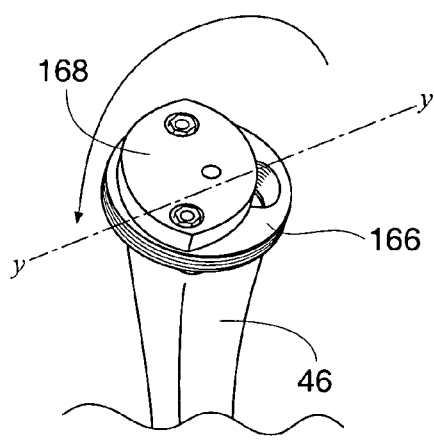
Figure 39D:
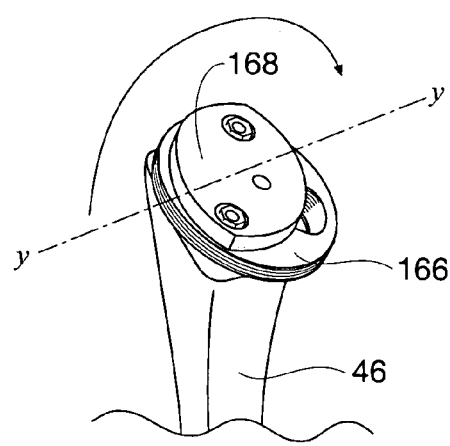

Second, as illustrated by arrows in FIGS. 39c–39d, the bottom plate 166 can be rocked or rotated, i.e., tilted, about the y-axis (i.e., front to back rotation).

Figure 39E:
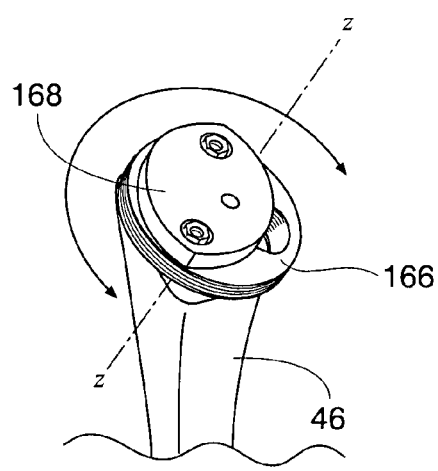

Third, as illustrated by arrows in FIG. 39e, the bottom plate 166 can be rotated up to 360° in either direction about the z-axis.

The slots 176 in the base 166 permit translation of the linear position of the major axis A1 and minor axis A2 with respect to the pivot pin 12 when the bottom plate 166 is slid along the x axis, providing a fourth degree of freedom, or the y axis, providing a fifth degree of freedom.

In assembling the system 10E, the post 120 is passed through the eccentric slot 174 of the bottom plate 166, thereby resting the ball 118 within the slot 174, as seen in FIG. 37. The bottom plate 166 is then slid (illustrated by arrows in FIG. 37) along the slot 174 until the desired lateral position is obtained. The fasteners 170 are then passed through the fixation slots 176 of the bottom plate 166.

Figure 38:
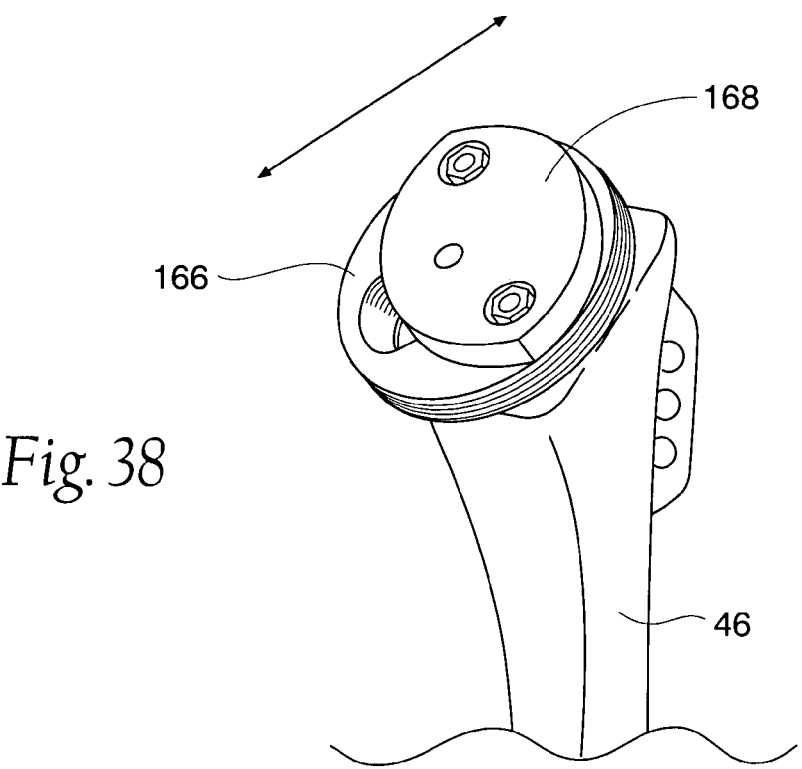
FIG. 38 is a view similar to FIG. 37 and illustrating the placement of the top plate on the bottom plate.

Next, the top plate 168 is aligned with the bottom plate 166 by aligning the recessed area 186 with the ball 118 and the fastener receiving holes 180 with the fasteners 170. The fasteners 170 are then passed through the fixation slots 176 of the bottom plate 166 and the fastener receiving openings 180 on the top plate 168. The top plate 168 is thereby positioned to rest on the ball 118 and over bottom plate 166, as FIG. 38 illustrates. The position of the plates 166 and 168 is then adjusted by rotating or rocking the bottom plate 166 about the x, y, and z axes (see FIGS. 39a–39e).

The components of the system 10E can be provided in a fully assembled form in which the user only need tighten the fasteners 170 after adjusting the position of the plates 166 and 168 to secure the plates 166 and 168 in the desired position.

Fastening elements 172, e.g., nuts, can be used if desired to tighten and secure the fasteners 170. This action compresses the plates 166 and 168 around the ball 118 to secure the plates 166 and 168 in the desired orientation and location relative to the ball 118.

Figure 40:
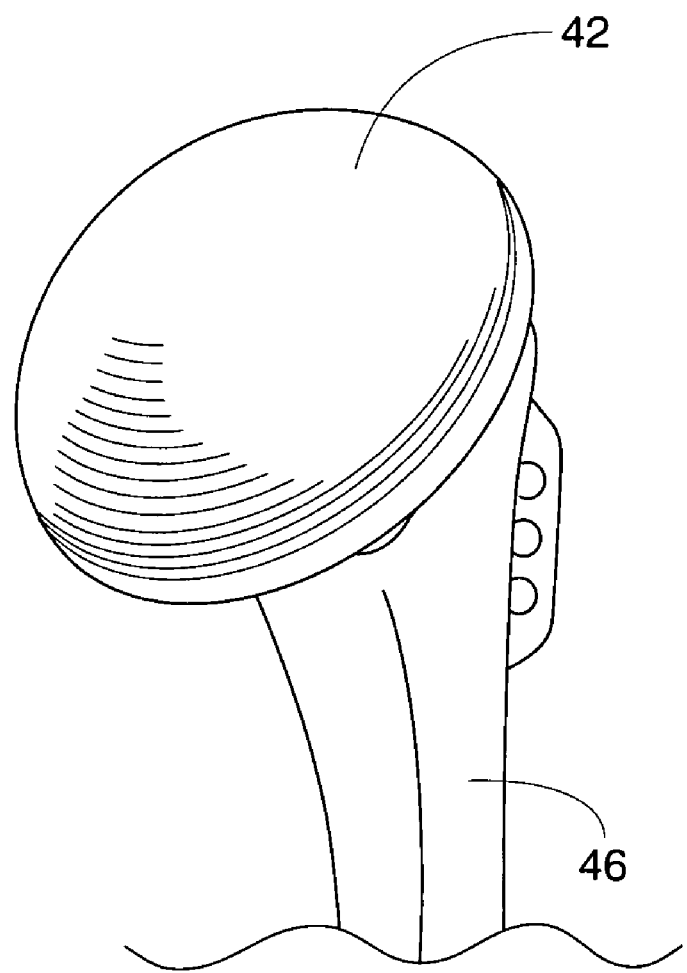
FIG. 40 is an assembled view of the system shown in FIGS. 35a and 35b.

Finally, as seen in FIG. 40, the head 42 is mounted onto the bottom plate 166.

The foregoing is considered as illustrative only of the principles of the invention. Furthermore, since numerous modifications and changes will readily occur to those skilled in the art, it is not desired to limit the invention to the exact construction and operation shown and described. While the preferred embodiment has been described, the details may be changed without departing from the invention, which is defined by the claims.

What is claimed is:

1. An assembly comprising
    a prosthesis,
    a support including a supporting surface,
    a mount including a mounting surface for the prosthesis, the mount being adapted to be supported by the supporting surface to permit relative movement between the mount and the supporting surface,
    a series of sequentially-stacked members including a first member, a second member, and a third member, at least one of the members being adapted for movement in concert with the supporting surface and not the mount and at least one of the members having a marginal edge adapted to engage an interior margin of the mount to permit movement in concert with the mount and not the supporting surface, the first member being carried by the mount and permitting relative movement between the first member and the mount, the second member being stacked sequentially above the first member and permitting relative movement between the second member and the first member, and the third member being stacked sequentially above the second member and permitting relative movement between the third member and the second member, the first and third members being sized and configured for movement in concert, the second member being sized and configured to not move in concert with either of the first and third members, and
    locking mechanism adapted for operation in a first mode to compress the first, second, and third members to create multiple concurrent frictional forces between the first, second, third members that limit movement of the mount upon the supporting surface and in a second mode to relieve the multiple concurrent frictional forces to allow movement of the mount upon the supporting surface for adjusting the position of the prosthesis.

2. An assembly as in claim 1
    wherein at least one of the members has a marginal edge adapted to be free from engagement with an interior margin of the mount to permit movement in concert with the supporting surface and not the mount.

* * * * *